US005560362A

United States Patent [19]
Sliwa, Jr. et al.

[11] Patent Number: 5,560,362
[45] Date of Patent: Oct. 1, 1996

[54] ACTIVE THERMAL CONTROL OF ULTRASOUND TRANSDUCERS

[75] Inventors: John W. Sliwa, Jr., Palo Alto; Michael G. Curley, Belmont; Donald R. Mullen, Fremont; Jay S. Plugge, Mountain View; Richard A. Lyon, Palo Alto, all of Calif.

[73] Assignee: Acuson Corporation, Mountain View, Calif.

[21] Appl. No.: 258,686

[22] Filed: Jun. 13, 1994

[51] Int. Cl.⁶ ........................................... A61B 8/00
[52] U.S. Cl. ............................ 128/660.03; 128/662.03
[58] Field of Search ................. 128/660.03, 662.05, 128/662.06, 4, 6; 607/92

[56] References Cited

U.S. PATENT DOCUMENTS

| | | | |
|---|---|---|---|
| 4,428,748 | 1/1984 | Peyman et al. | 606/171 X |
| 4,586,512 | 5/1986 | Do-huu et al. | 128/660.03 |
| 4,748,985 | 6/1988 | Nagasaki | 128/4 X |
| 4,889,112 | 12/1989 | Watmough et al. | 607/97 |
| 5,213,103 | 5/1993 | Martin et al. | 128/661.01 X |
| 5,240,675 | 8/1993 | Wilk et al. | 128/4 X |

*Primary Examiner*—Francis Jaworski
*Attorney, Agent, or Firm*—William F. Prendergast; Brinks Hofer Gilson & Lione

[57] ABSTRACT

An ultrasound transducer assembly having a housing, a transducer array mounted in the housing, and active cooling mechanism positioned adjacent to the transducer array for actively removing heat generated by the array by transport of heat energy from the affected site. The active cooling mechanism may comprise a heat exchanger including a closed loop circulating coolant system circulating coolant, or a single-pass flowed coolant, passing through the heat exchanger, a heat pipe, a thermoelectric cooler, an evaporative/condenser system, and/or a phase change material. One or more heat exchangers may be used having gas or liquid coolants flowing therethrough. The heat exchangers and coolant pumps may be located in various components of the transducer assembly, including the array housing, the connector assemblies or the ultrasound console.

107 Claims, 13 Drawing Sheets

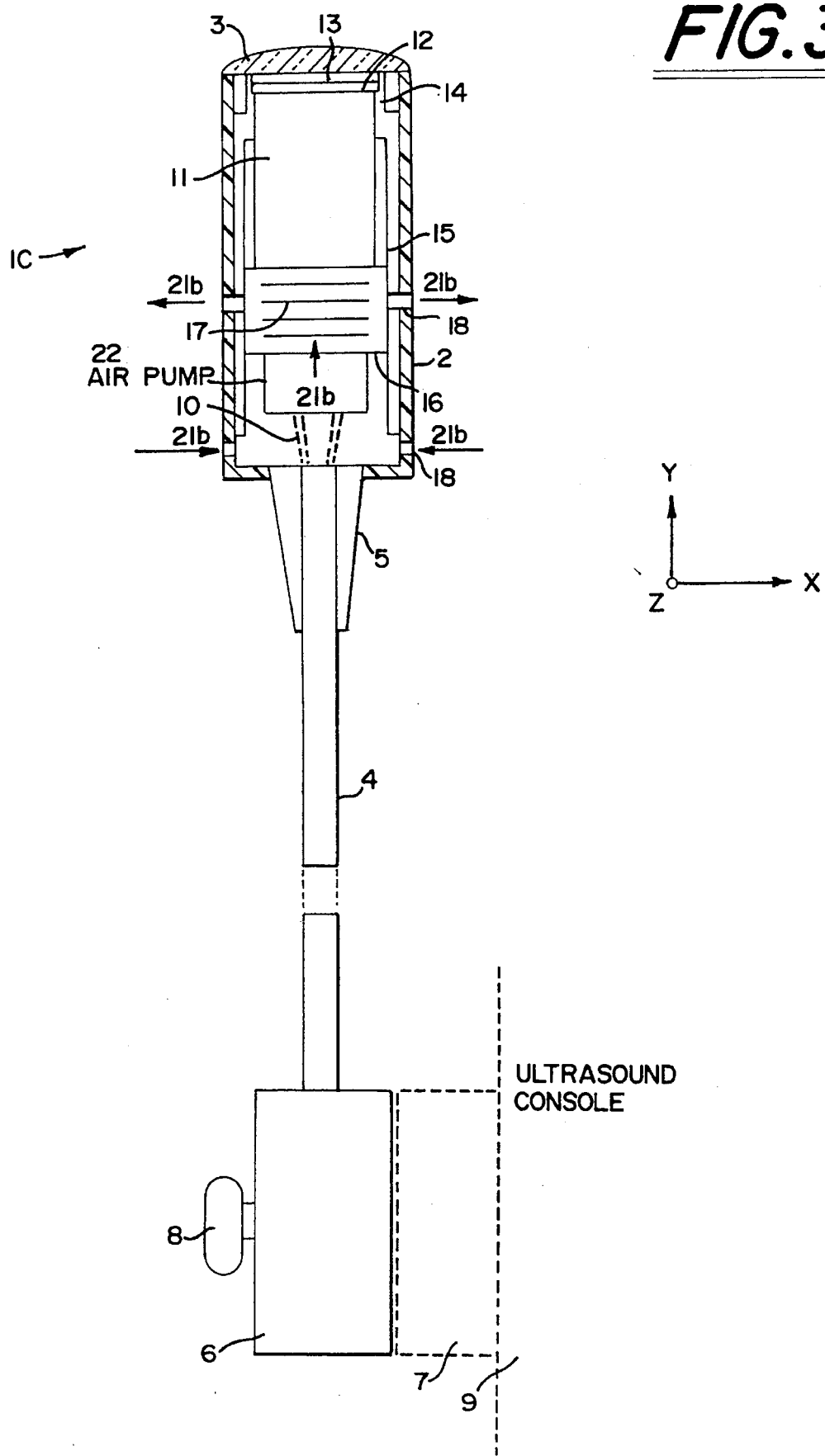

ACTIVE THERMAL CONTROL OF ULTRASOUND TRANSDUCERS

BACKGROUND OF THE INVENTION

1. Field of the Invention

The invention relates to imaging of materials in living tissue, and in particular to increasing the power output of transducing means used for acoustic imaging by compensating for thermal problems associated with such increased power output.

2. Description of the Related Art

Medical ultrasound imaging has become a popular means for visualizing and medically diagnosing the condition and health of interior regions of the human body. With this technique an acoustic transducer probe, which is attached to an ultrasound system console via an interconnection cable, is held against the patient's tissue by the sonographer whereupon it emits and receives focused ultrasound waves in a scanning fashion. The scanned ultrasound waves, or ultrasound beams, allow the systematic creation of image slices of the patients internal tissues for display on the ultrasound console. The technique is quick, painless, fairly inexpensive and safe, even for such uses as fetal imaging.

In order to get the best performance from an ultrasound system and its associated transducers it is desirable that the transducers used to emit and receive ultrasonic pulses be capable of operating at the maximum acoustic intensity allowable by the U.S. Food and Drug Administration (FDA). This will help maximize the signal to noise ratio for the given system and transducer, help achieve the best possible acoustic penetration, and ensure that imaging performance is not limited by the inability to emit the full allowable acoustic intensity. At the same time, there are practical and regulatory limits on the allowable surface temperature that the transducer may attain as it performs its imaging functions. The Underwriters Laboratory (U.L.) Standard #UL544 "Standard for Safety: Medical and Dental Equipment" specifies an upper limit of 41° C. for the transducer portion contacting the patient's skin. In addition, sonographers prefer to grip a transducer case which is comfortably cool, thereby preventing excess perspiration in their hands and a potential to lose their grip on the device.

Given that it is desirable to be able to operate at the maximum allowable acoustic intensity and also desirable to control the surface temperature distribution of the patient and user-contacting portions of the transducer's surfaces, thermal engineering is a serious consideration during transducer design. There are essentially two possible paths to proceed on with regard to transducer thermal engineering.

The first path makes use of passive cooling mechanisms and involves insuring that the heat that is generated both by the electroacoustic energy conversion process taking place in the transducer's piezoelements and by the acoustic energy passing through and/or into adjacent transducer materials is passively spread out to as large an external transducer surface area as possible. This heat spreading process is typically achieved internal to the transducer by thermal conduction through solid materials and subsequently from the transducer's external case employing natural free convection to the atmosphere. Ideally the external heat-convecting surface area would consist of the entire transducer's external surface area from which free convection cooling to the atmosphere can potentially take place in an unobstructed manner. Transducer manufacturers have thus incorporated various passively conducting heat-spreading plates and members inside the transducer's interior spaces to ensure the spreading of the heat to the entire transducer case surface. Such members work well, however, it is frequently the ability to get the heat out of the electroacoustic elements themselves and into such adjacent internal thermal-sinking structures such as these commonly used spreading plates that provides a significant portion of the probes total thermal dissipation resistance. If this internal thermal path is not a good one it is difficult to spread the heat generated by the piezoelements around the case. If the heat generated by the piezoelements cannot be removed, and effectively coupled and sunk to the entire transducer case area, then the probe surface portion in contact with the patient runs hotter than desired as this probe portion is directly adjacent the piezoelements. Thus, even in the passive strategy, there is concern concerning three key mechanisms: a) removing the heat from the highly localized piezoelement region; b) spreading said heat efficiently to the external case surfaces; and c) allowing for unobstructed natural convection from the warm transducer surfaces.

In any event, using this passive strategy, maximizing the external probe surface area onto which heat spreads in a fairly uniform manner minimizes the peak surface temperature attained anywhere on the probes surface during steady state convection of the probes heat to the ambient. This passive strategy amounts to spreading the heat load around to minimize the impact of the limited ability of free convection to dissipate heat. Its fundamental limitation is that, for most transducers, even if heat is spread uniformly on the external case surfaces, it only takes a few watts of transducer driving power to cause the average transducer surface temperature to become unacceptable either with respect to the patient or the sonographer. In these cases, and particularly for small transducers having small surface areas, one may find that one is unable to operate at the allowable acoustic intensity limit because of excessive temperatures.

FIG. 1 shows a prior-art medical ultrasound transducer 1 in schematic sectional view. Transducer 1 has a typically polymeric external case 2 which is gripped by the sonographer. The top of the transducer (+Y end) can be seen to have the typical acoustic lens 3 which serves to focus the ultrasound beam in the X-Y plane as it passes into the subject patient. Focusing in the Y-Z plane is done via electronic phase delays between the various piezoelements which are arranged on a Z-axis pitch and spacing passing into and out of the paper as is usual for phased array transducers. The bottom or back of the transducer 1 has emanating from it a flexible coaxial cable bundle 4. The cable 4 is shown in broken view at its midpoint to indicate its considerable length, usually on the order of 6 to 12 feet. Where cable 4 exits from the transducer 1, and specifically where it exits from the transducer case 2, can be seen a flexible strain relief 5. Strain reliefs are usually fabricated from a flexible rubber, such as silicone rubber, and they serve to prevent damage to the cable 4 or chemical leakage into the case 2 at the point of cable/case juncture particularly as cable 4 is flexed by the user.

A transducer cable connector 6 can be seen at the termination of the cable 4 (−Y end). The connector 6 is usually of a mass-actuated design and has an appropriate rotatable actuation knob 8 for that function. To the right of the transducer's connector 6 are shown in phantom a mating ultrasound system connector 7 mounted on an ultrasound system console 9. To use the transducer the sonographer would plug connector 6 into mating connector 7 (connectors shown unmated) thereby electrically connecting the transducer 1 to the ultrasound system console 9.

In the interior portion of the bottom of transducer 1, inside of polymeric case 2, portions of numerous electrical interconnects 10 (indicated by partial dotted lines) run from the transducer device 1 into the cable 4 and, in turn, into the connector 6. Generally a large number of interconnects 10 comprising coaxial wires of controlled impedance are provided in cable 4 to carry the electrical impulses transmitted to and received from the individual piezoelements making up the phased array. The details of how the interconnects 10 are mated to the piezoelements or to the connector are not shown as it is not critical to the understanding of this invention. It should be generally understood that numerous interconnects 10 pass from the transducer 1 and its piezoelements through the cable to the connector 6 and these serve an electrical function. Interconnects 10 must physically be routed through the interior of the back of the transducer case 2, and around whatever other means, thermal or otherwise, are located therein.

The electroacoustic transducer device assembly 50 is packaged and operated inside the confines of the polymeric case 2. Assembly 50 is shown schematically in FIG. 1 and in FIG. 7a. Assembly 50 comprises acoustic backer material 11, a piezoelements 12 and one or more (one shown) acoustic matching layers 13. Acoustic backer material 11 serves the functions of attenuating acoustic energy which is directed backwards to minimize reverberations and ringiness, and as a mechanical support for piezoelements 12. Materials used to fabricate backer 11 are generally poorly or only modestly thermally conductive as it is exceedingly difficult to design a highly thermally conductive yet acoustically highly lossy material. Piezoelements 12 may, for example, be fabricated from lead zirconate titanate (PZT) or composite PZT in a manner well-known to one of average skill. On top of piezoelements 12 is the matching layer or layers 13 which serve to act as an acoustic impedance transformer between the high acoustic impedance piezoelements 12 and the low acoustic impedance, human patient. (The human patient is not shown, but it should be understood that the patient is in contact with lens 3.)

The piezoelement material, typically PZT, is a ceramic having generally poor to modest thermal conductivity. The matching layer(s) 13 materials also frequently have poor to modest thermal conductivity because of their conflicting acoustic requirements. It is to be noted that the backer 11, the piezoelements 12 and the matching layer(s) 13 are all intimately bonded to each other and to the lens material 3 such that acoustic energy produced in piezoelements 12 may pass through the layer interfaces in the +Y-direction freely. Of course reflected acoustic echoes from the body may also likewise pass freely in the −Y direction, back into probe 1.

Not shown in FIG. 1 are horizontally running (+−X axis direction) electrodes in any of the interfaces of the type between lens 3 and layer 13, layer 13 and piezoelements 12 or piezoelements 12 and backer 11. Adequate thin electrodes must be present to apply and sense electrical potentials across the top and bottom surfaces of the piezoelements 12. Electrical interconnects 10 are typically routed and connected to such dedicated interface electrodes on a piezoelement by piezoelement basis (connections and routing not shown). The interface or surface electrodes are required to make electrical contact to each piezoelements 12 without appreciably negatively impacting the acoustic performance spectrum of transducer 1. Thus, such electrodes are typically chosen to be very thin, metallic, and have very little mass. This, in turn, causes the electrodes to be poor thermal conductors in the lateral X-direction.

Also shown in FIG. 1 are two symmetrically situated pairs of passive thermal conduction enhancement members 14 and 15 arranged on each side of assembly 50. Thermal member 14 is schematically shown physically and thermally connected to the edge region of element array 12 and layer 13, and possibly also to the ends of the interfacial or surface electrodes (not shown). Thermal member 15 is schematically shown thermally and physically connected to member 14. The members 14 and 15 are arranged to be in close juxtaposition and in good thermal contact with the interior walls of case 2. It will be noted that thermal member 15 may typically be thicker (as shown) and therefor more thermally conductive than member 14 given the increased space toward the cable end of the transducer. In one such representative example, items 14 would consist of thin films of flexible copper, perhaps in the form of a flexible circuit, extending away from the edges of the piezoelement array 12 and possibly emanating from within an interface such as the interface between backer 11 and array 12, array 12 and layer 13 or layer 13 and lens 3 wherein it also serves an aforementioned electrode function. In this example, the primary purpose of member (or flex circuit) 14 is electrical interconnection as necessary in the interfaces between at least certain of the laminated layers. Items 15 would typically consist of aluminum or copper plates, perhaps between 0.010–0.080 inches thick, which are bonded or thermally coupled intimately to the inner surfaces of case 2. The joint between members 14 and 15 must be thermally conductive. If member 14 is an electrical flex circuit used for interconnection, then care would be taken to provide only a thermal joint and not an electrical joint so as not to short out the flex traces which need to be routed (not shown) backwards to interconnects 10.

As the sonographer or user images with transducer probe 1, the system console 9 transmits a series of electrical pulses through the connectors 7,6 and cable 4 to the acoustic array of piezoelements 12. The electroacoustic piezoelements 12 convert the electrical pulses to acoustic output energy emanating from the rubber lens 3 into the patient. During the ultrasound reception portion of the acoustic beamforming, the piezoelement senses in a passive mode the electrical disturbance produced by acoustic energy bounced off of internal patient tissue and reflected back into the transducer 1. It is primarily the transmit portion of imaging when heat is produced by the piezoelements. This is because the electroacoustic energy conversion process is less than 100% efficient. Thus the piezoelements 12 act as unintended heaters. Secondly, as ultrasound energy is produced by the piezoelements 12, it is somewhat absorbed by layers 13 and lens 3, such layers usually not being totally lossless. The unavoidable nonzero portion of acoustic energy which is directed away from the patient into the backer 11 also serves to generate heat in backer 11. Thus, we have heat being directly generated in the piezoelements 12 and indirectly generated in backing material 11, matching layer(s) 13 and lens 3.

A thermal member 14, if comprised of a flexible circuit being formed in part of a thin metal such as copper, offers modest thermal conduction of heat generated by piezoelements 12 laterally in the X direction to the edges of the device and then downward to some more significant thermal sink, such as 15. The purpose of member 15 is to render isothermal the inner surface of the case 2 so that heat may be encouraged to flow across the case wall at all locations. The thermal purpose of member 14 is to get the heat away from the piezoelements 12 and redirected so that it can be flowed into said isothermalization member 15. Using the combination of thermal elements 14 and 15 it has been possible to passively spread the heat out isothermally to most of the interior case 2 surfaces. It should be understood that case 2, being fabricated of a polymer, will typically conduct heat poorly. It is therefore critical to get the heat spread out over most or all of the interior surface of case 2 so that although the thermal resistance across the thickness of the case wall 2 is high, there is considerable surface area to compensate for this fact and keep the overall thermal resistance between the elements and the environment as low as possible.

Heat which is generated in matching layer(s) 13 and lens 3 may also be conducted downward toward the piezoelements 12 or to their interfacial electrodes (not shown) which can, in turn, pass heat to the edges of the stack for redirection downward in the −Y direction via member 14 for example. When transducer probe 1 is in contact with a patient's tissue, some heat may pass directly into the patient. In any event, the U.L. limitation on skin or tissue temperature severely limits the temperature of the lens, and heat dissipation toward the patient.

Heat which is generated in backing material 11 may be passed to thermal means such as member 15. Member 15 may be arranged to actually envelope or wrap around backer material 11 in the form of a metallic thermal container or can (not shown) in order to facilitate the passage of heat from backing material 11 into thermal member 15 and out of transducer 1.

Thus, the ability of probe 1 to shed heat to the environment is governed primarily by passive free convection of heat from the probe's external surfaces. There is a rather limited capacity to remove heat by natural convection of air past the external probe surface even in this optimal isothermalized example. In practice, given the limits on the temperature of lens 3 and sonographer gripping comfort, it is not possible to dissipate more than a few watts of thermal energy in this passive prior-art manner. Also, different sonographers typically cover different amounts of the probe surface with their hands as they grip it, and in some cases much of the heat is being transmitted by conduction directly into the sonographer's hand(s). This can produce sonographer discomfort and a poor grip. If the only heat dissipating surface and path available is the external case surface dissipating by convection to the atmosphere or by conduction into the patient and/or the sonographer's hand, then severe power dissipation limits of a few watts will apply, particularly to small probes having small surface areas even if that surface area is isothermalized.

Others have attempted to increase the lateral (X-axis) and/or vertical (Y-axis) thermal conductivity of acoustic backing material 11, piezoelements 12 and acoustic matching layers 13. Although these measures may help keep the face of the acoustic array more isothermal particularly for very large array probes, they do nothing to increase the capacity to remove heat from the probe's external surfaces in an improved manner.

An extension of the passive-cooling approach has included an attempt to conduct or spread some of the heat down the length of the attached cable in order to permit the cable to offer more passive convection surface area. This helps the situation only incrementally because of the user-preferred small diameter cable and the difficulty of providing much of a thermally conductive path in such a small diameter cable without compromising the desired flexibility and compactness of the cable. Such an incremental measure is described in U.S. Pat. No. 5,213,103 "Apparatus for and method of cooling ultrasonic medical transducers by conductive heat transfer" by Martin, et al.

As a specific example a copper braid could be routed from the case 2 interior into at least some limited length of the cable 4 adjacent to device 1. This copper braided thermal means may be connected to a thermal means in the case such as depicted member 14, 15 or 14 and 15 or may also serve as item 15 for example. This tact essentially creates additional dissipative surface area on the cable.

It should be noted that for endocavity transducers (probes inserted internally into the human body) heat is dissipated both by direct conduction to the patient's internal tissues and fluids, as well as by the conduction out the cable and convection from the exposed transducer handle which remains external to the patient's cavity. We must also control the maximum surface temperatures attained by these probes.

The second strategy for cooling transducers, which, to the knowledge of the inventors, has not yet been pursued by any medical ultrasound vendor, is to utilize active cooling rather than passive cooling in order to dissipate heat well beyond that which can be passively convected or conducted from the external transducer surfaces. Active cooling means that one provides a means to actively remove heat from the transducer such as by employing a pumped coolant or other active refrigeration means. Using active cooling one may ensure that one is always able to operate the acoustic transducer up to the allowable acoustic intensity limit while also maintaining acceptable surface temperatures regardless of how small the transducer is or how much surface area it offers for cooling relative to its acoustic intensity.

At least part of the reason active cooling has not yet been used is because of the apparent cost, reliability and the ease-of-use issues associated with it. There is a well-established continued trend in the ultrasound industry toward reliable "solid-state" phased array transducers with no moving parts and with excellent chemical resistance to disinfection procedures, including procedures involving total chemical immersion for extended periods. There is a more recent trend toward minimizing the cost of ownership for all medical implements as well as any need to service or repair them. Both of these trends place very severe constraints on any potential active transducer cooling means for use in the hospital, clinic or doctor's office environment.

Finally, one must keep in mind that imaging transducers are plugged into and unplugged from the ultrasound console's various connector ports in a varying personalized manner, thus any active cooling scheme should preferably continue to allow for the freedom to do this and should not substantially complicate the integrity or ease of this connection. Large numbers of connector plug/unplug cycles should also not degrade the performance of the active cooling means. Any active cooling scheme should involve minimal additional maintenance and should be as transparent to the user as possible.

SUMMARY OF THE INVENTION

It is an object of the invention to provide an active transducer cooling arrangement, utilizing actively flowed coolants of various types.

A further object of the invention is to provide a plurality of active cooling embodiments, wherein each design represents a novel and reasonable balancing of the many constraints mentioned above.

It is an additional object of the invention to specify designs which allow for the local removal of transducer heat using a solid state thermoelectric cooling device which is electrically actively driven.

It is a further object of this invention to specify designs which utilize semi-active, heat-pipe technologies to efficiently transport and redistribute heat and, if desired, to also control temperature.

It is another object of this invention to specify additional designs which allow for generated heat to be temporarily stored.

It is an additional object of this invention to offer a passive thermal-conduction enhancement means to conduct away from the electroacoustic elements such that any thermal means, including the passive prior art means and/or the active means disclosed herein, may transport the heat efficiently away from the transducer.

These and other objects of the invention are provided in an ultrasound transducer assembly having a housing, a transducer array mounted in the housing, and active cooling means positioned adjacent to the transducer array for actively removing heat generated by the array by transport of heat energy from the affected site.

The active cooling means may comprise a heat exchanger including a flowed coolant in a closed-loop, multipass circulating coolant system or single-pass flowed coolant, the coolant passing through the heat exchanger, a heat pipe, a thermoelectric cooler, an evaporator/condenser system, and/or a phase change material.

In embodiments employing heat exchangers, one or more heat exchangers may be used having gas or liquid coolants flowing therethrough. Open, single-pass and closed-loop, multi-pass coolant systems may be used. The heat exchangers and coolant pumps may be located in various components of the transducer assembly, including the array housing, the connector assemblies or the ultrasound console.

It will be recognized by one skilled in the art that the active and semiactive means disclosed herein may be driven or allowed to operate as part of a feedback loop wherein a probe temperature is maintained at a desired level or below a limit value. In such a feedback scheme temperature would be sensed and that data used to determine the extent of the application of the active or semiactive cooling or thermal control means to achieve the thermal goals of the product as it operates.

It will also immediately be recognized by those skilled in the art that one may easily use the temperature control means to also heat the probe such that it is warm and comfortable to the patient's touch when first used. Alternatively one might ensure that the probe operates at all times at a desired temperature setpoint (including when the probe is first switched on) or below such a setpoint or above a lower setpoint and below a second higher setpoint. Any scheme wherein heating is involved would include adding a heater means to our described coolant loops. The thermal control means might also be used to cool the probe to prevent damaging it during hot disinfection or sterilization procedures used to clean the probe.

A further embodiment includes implementing improved passive thermal conduction materials for coupling to standard passive thermal conductors and/or active means. In one such embodiment, liquid-filled deformable bags are provided within the transducer which efficiently couple heat between irregular surfaces, but allow for easy disassembly for servicing of heat-dissipating electronics in the transducer.

BRIEF DESCRIPTION OF THE DRAWINGS

The invention will be described with respect to the particular embodiments thereof. Other objects, features, and advantages of the invention will become apparent with reference to the specification and drawings in which:

FIG. 2b is a partial cross-sectional view of a second embodiment of a device in accordance with the present invention similar to the arrangement of FIG. 2a but where the gaseous coolant, such as air, is instead drawn into the probe and passed along the cable toward the console in the opposite direction to that of FIG. 2a.

FIG. 3a is a partial cross-section of a third embodiment of a probe device in accordance with the invention wherein the probe contains a heat exchanger for active cooling and a miniature fan or other coolant-moving pump means to forcibly pass coolant by a probe heat exchanger.

DESCRIPTION OF THE PREFERRED EMBODIMENTS

Figure 1:
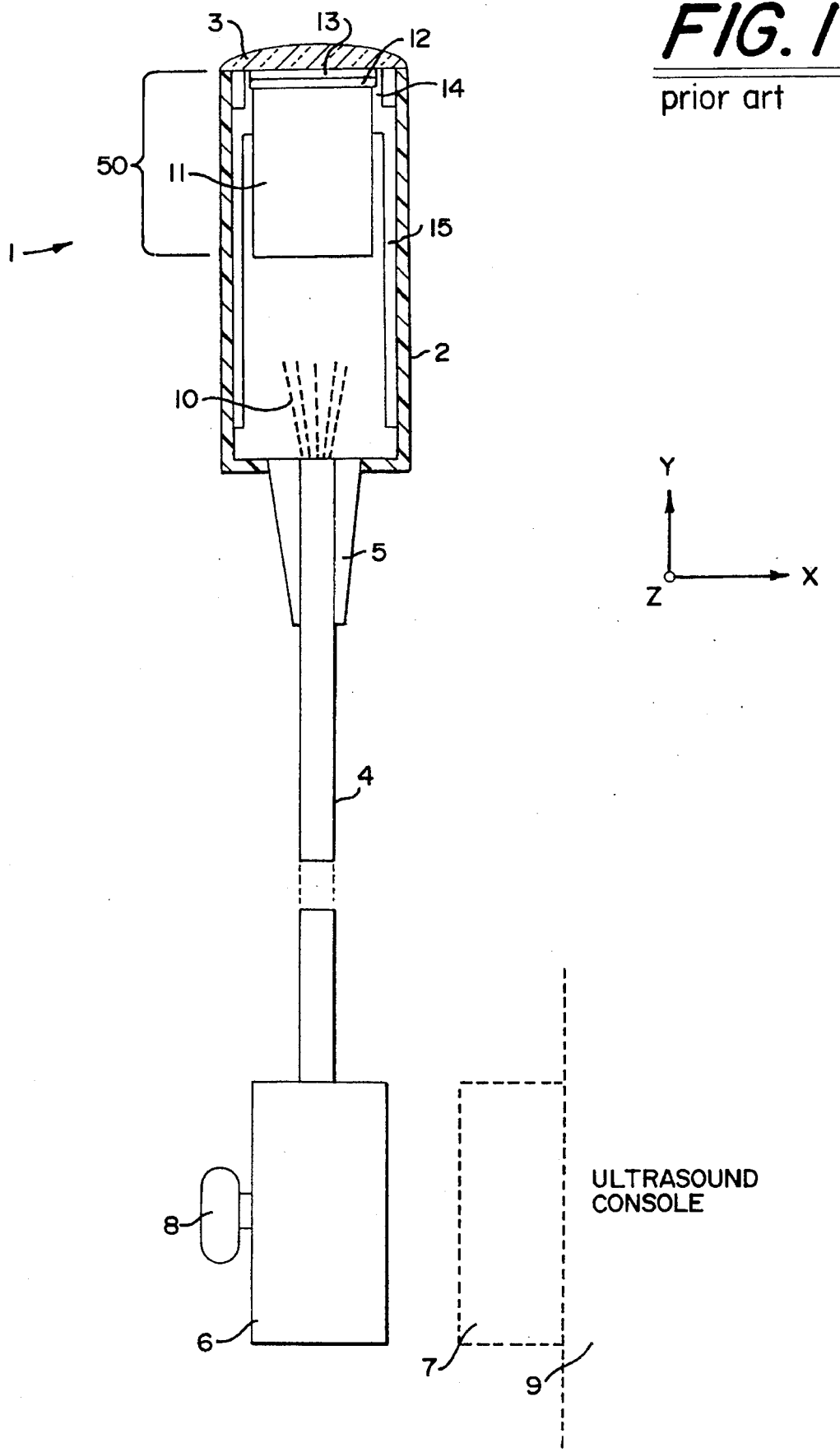
FIG. 1 is a partial cross-sectional view of a typical industry-standard, solid-state, phased array transducer with its accompanying cable, system connector, system-console, mating connector, and typical passive heat distribution plates.
Figure 2A:
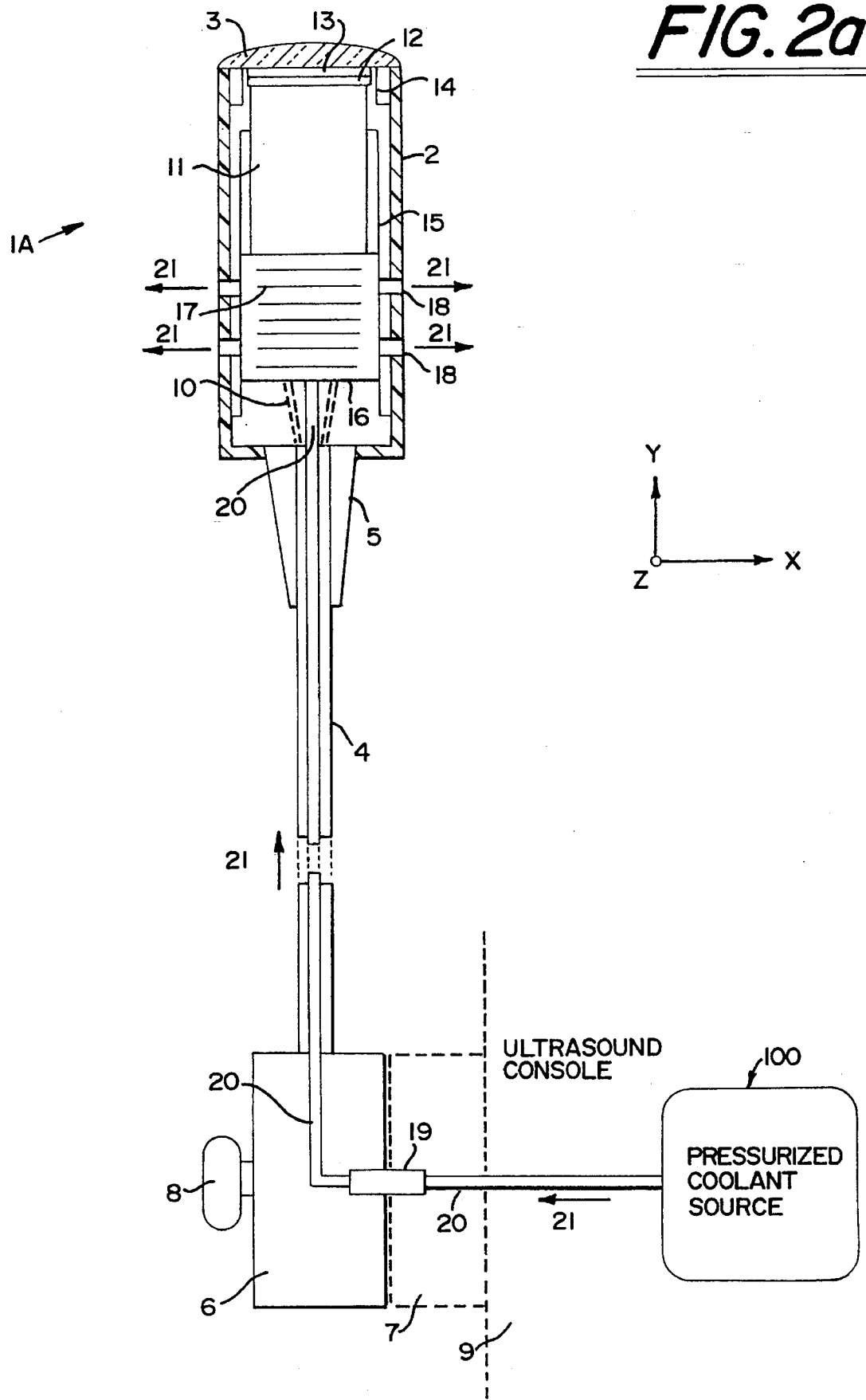
FIG. 2a is a partial cross-section of a first embodiment of a device incorporating the active cooling elements in accordance with this invention wherein a gaseous coolant, such as air, is forced by pumping or pressurization means located at or near the connector/console end of the transducer cable through the cable into the device.

FIG. 2a shows a first embodiment of the invention which is generally externally similar in overall structure to the transducer probe 1 shown in FIG. 1. Elements in probe 1 and 1A having like construction are designated with the reference materials set forth in FIG. 1. Probe 1A of FIG. 2a includes a heat exchanger 16 having internal heat exchange fins 17. It will be noted that there is a flow of coolant gas 21 into heat exchanger 16 from tube 20 in cable 4. Exhaust or coolant gas exit ports 18 vent the coolant gas 21 to the atmosphere after it has absorbed heat from heat exchanger 16 and fins 17. It will be noted that the heat exchanger 16 is arranged to be in intimate thermal contact with the passive thermally conductive members 15.

Referring to the lower portion of FIG. 2a, it will be noted that the connectors 6 and 7 are shown mated and that the gas delivery tube 20 is connected in continuous fashion through the coupled connector portions 6 and 7 and into the system ultrasound console 9. A coupling fitting 19, such as a snap-lock pneumatic fitting with an O-Ring, is shown providing a generally airtight connection between the portions of tube 20 and the connectors 6 and 7. Connector 19 would most likely have a male and a female portion wherein the male portion is mounted to either connector 6 or 7 and the female portion to the remaining connector. When the connectors are mated electrically, they are thus also mated pneumatically in a manner to connect the gaseous coolant source in the system to the probe. Inside the system console 9 is a pressurized coolant source 100 whose positive pressure forces gaseous coolant in the form of flow 21 through tube 20 toward and into case 2.

Transducer 1A would not be subject to liquid coolant spills, dripping connections, or coolant fluid level monitoring when a gaseous coolant is used. Air is an advantageous gaseous coolant because it does not necessarily have to be provided in the form of a tank or reservoir as with bottled gases. Instead, the indicated pressurized coolant source 100 may consist of a compact and efficient air pump of any design desired, including positive displacement designs, turbine designs, rotor designs and fan designs. The air being pumped by the pressurization source would be drawn from the environment in these cases. However, by pressurized coolant source we broadly mean any possible source of pressurized gas, including pressurized air bottles (cylinders) or bottles of any other gases such as nitrogen or helium.

Although FIG. 2a shows a pressurized gas source in the system console 9, one may alternatively place the gas source means in connector 6, in connector 7 or even external to the probe/cable/connector/console hardware. In any event, a tube or conduit of the type 20 will be provided in a manner which causes the sonographer minimal inconvenience. It will be noted that for the design shown in FIG. 2a, the sonographer does not physically see any component of the coolant system. Also, the least reliable portion of the cooling system which might need repair is the pressurization source 100 which is located in the system 9 (or alternatively in connectors 6 or 7) where it can be serviced without disassembling the transducer probe 1A. By placing the pressurization source or pump 100 in the console 9, a purchaser need not repeat that investment when he/she buys additional transducers at later points in time.

In FIG. 2a, exhaust ports 18 are shown on the sides of probe case 2. These exhaust ports may alternatively be placed anywhere, and may be connected to the heat exchanger via additional conduit or tubing (not shown). In order to minimize pressure drops, it is typically best to minimize the length of the tubing; the design shown achieves this by directly dumping the heated gas to the environment. One may utilize filters, mufflers, and/or gas diffusers (not shown) to keep the gas clean so as not to foul the internal coolant paths, so as to silence or muffle flow noise and so as to redirect or spread out the exiting gas stream such that it does not bother the sonographer in any way.

If the pressurized gas source 100 is external, the gas delivery conduit or tube 20 may enter the probe at a location other than emanating from the interior of cable 4. Yet another alternative to this approach includes providing heat exchanger 16 on the outside of case 2 along with conduit 20, where each may be electively detached. In all of these cases, a heat exchanger 16 is provided at the transducer 1A and connected to a gas source 100 outside of the transducer 1A.

In general, using the approach indicated in FIG. 2a, one may, with reasonable gas source pressures of 40–100 psi, handle 4–20 watts depending on the diameter of tube 20, the length of tube 20, the size of the heat exchanger 16, and the maximum allowable level of flow noise. In most ultrasound cables, a high pressure flexible tube 20 having a diameter of approximately 0.050–0.125 inches is suitable for use. Tube 20 may be fabricated of polyimide, for example, in which case a fairly thin wall thickness of from 0.004–0.012 inches may be used. Easily coupled gas fittings 19 are also readily available, including those from the product lines of Swagelock Company (31400 Aurora Road, Solon, Ohio 44139), Parker Hannifin Corporation (8145 Lewis Road, Minneapolis, Minn. 55427), and Colder Products Company (1001 Westgate Drive, St. Paul, Minn. 55114).

Figure 2B:
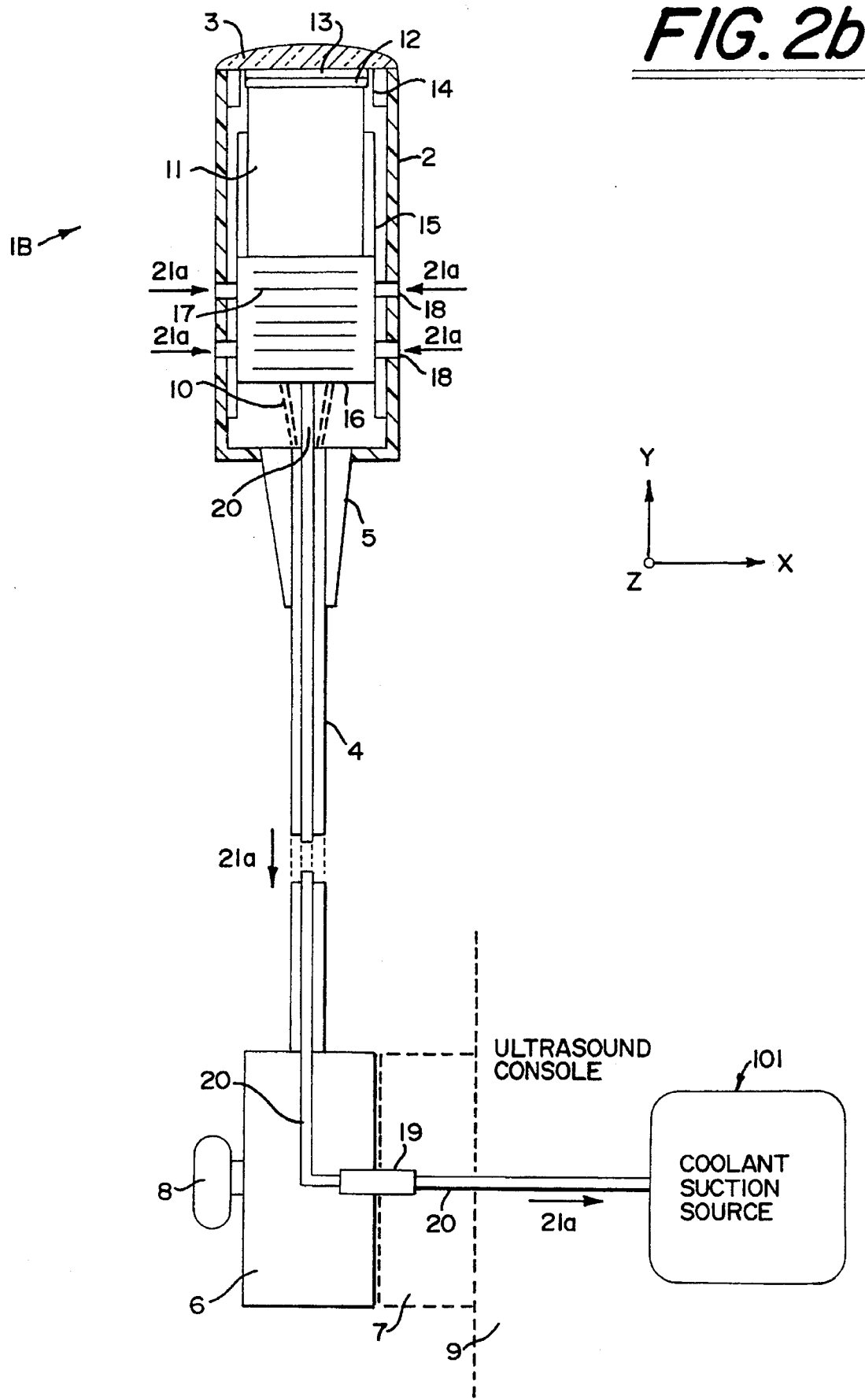

FIG. 2b shows a second embodiment of the invention. In general, this embodiment is similar to the embodiment shown in FIG. 2a, however the coolant gas 21A is flowing in the opposite direction from that disclosed in FIG. 2a—i.e., into the transducer probe 1B, through heat exchanger 16, into tube 20, through connector halves 6 and 7, and into ultrasound console 9 and a coolant suction source 101. Coolant suction source 101 may be any convenient suction or negative gauge pressure source such as a compact vacuum pump, suction pump, vane pump, rotary pump or positive displacement pump.

An advantage of this arrangement over that of FIG. 2a is that one does not have to deal with warmed exhausted coolant gas at the probe which may, on occasion, be a noise problem, a comfort problem or might disturb a surgical site. A disadvantage relative to FIG. 2a is that one may only apply one atmosphere of gage suction pressure or about 14.7 psi wherein the FIG. 2a device may utilize several tens of pounds of positive pressure. In a manner similar to that for FIG. 2a the pumping device, in this case the suction source 101, may be placed closer to the probe 1 such as in connector half 6 or 7 or elsewhere externally to the probe/cable/connector/console. Tube 20 may also be routed directly to the probe case 2 from other than the cable 4 interior.

For both FIGS. 2a and 2b the exact means of thermally coupling, either directly or indirectly, exchanger 16 to the heatflow from the electroacoustic elements 12, is unimportant. Heat flow passing from the dissipating elements 12 to a passive thermally conducting member 14, then to a passive thermally conducting member 15, then into the heat exchanger 16 and thus into the gas stream 21 or 21A is depicted. In most cases, the designer will strive to get the exchanger 16 as close to dissipators 12 as is physically possible so as to minimize the overall thermal resistance between the element dissipators 12 and the atmosphere.

Note that a "finned" heat exchanger 16 having internal "fins" 17 has been described. It is to be stressed that included in the scope of this invention is the use of any heat exchanger capable of passing heat into a passing gas stream. For example, one might utilize a heat exchanger based on an array of metal tubes, an array of metal pins or even a porous metal. "Heat exchanger" is herein defined as any means, including any directly associated containments necessary to direct the coolant flow over the fins or their equivalents, which can pass heat from an adjacent coupled heat source to a forced or pumped coolant stream. Thus one might even choose to utilize components 11,12,13 or 14 for example to not only do their previously described prior art acoustic and structural functions, but to also serve the function of a heat exchanger. As an example, piezoelements 12 are many in number and are arranged on a pitch in the Z axis to achieve their basic acoustic array function. Their arrangement is actually much like an array of fins and one may thus force the coolant gas through them (through the spaces or kerfs between them) to form a heat exchanger 16 integrated directly and intimately with the acoustic means. In this case, a fin 17 may itself be a heat producing piezoelements 12. A more common case of partial integration of exchanger 16 would be where the portions of the case 2 serve to direct and contain the coolant flow over metal fins 17.

It should also be noted that one may choose, for either of the designs 2A or 2B, to route the exhausted coolant gas (exhausted from the heat exchanger) all the way back to the connectors 6,7, or ultrasound console 9, in an additional tube or conduit 20 running inside or along the outside of the cable 4 (not shown). Such approaches would provide an additional pressure drop, as well as undesirable preheating of the incoming coolant gas if the ingoing and outgoing coolant-gas tubes are in thermal communication over their considerable length. Nonetheless, one may implement the FIG. 2a–b systems as closed-loop systems, as long as the heat can be extracted from the coolant before it is returned to the probe.

Specific pressurization/suction means 100 and 101 suitable for use with the embodiments shown in FIGS. 2a–2b include the following: EG&G Rotron (7 Hasbrouck Lane, Woodstock, N.Y. 12498), Gast Manufacturing Corporation (2300 Highway M-139, Benton Harbor, Mich. 49023-0097), and Ametek (627 Lake Street, Kent, Ohio 44240) offer regenerative continuous flow blowers which can generate 10–100 inches of water-pressure head or suction column; and Medo U.S.A., Inc. (808-A North Central Avenue, Wood Dale, Ill. 60191) offers positive displacement interrupted flow pumps which can generate very high pressures. It is to be understood that the addition of checkvalves, pressure (or vacuum) accumulators, pressure controllers, throttling valves, on/off valves or other auxiliary flow-control or monitoring item to the cooling systems herein described may be necessary. The list of exemplary pump means 100 and 101 is in no way exclusive, as there are literally hundreds of pump, pressurization and suction means available in a variety of engineering disciplines.

FIG. 3a shows a third embodiment of the invention. In this embodiment, the source of the gas pressure difference driving the flow (the pressurization or suction means) is relocated to the interior of the transducer probe case 2. FIG. 3a shows an air pump 22 (a pressurization source) inside of case 2 or probe 1C. Air 21B is drawn into the probe from the environment through ports 18 at the back of the probe by the internal air pump 22. Air pump 22 is shown forcing the air stream 21B into the heat exchanger 16 and through its internal fins 17. Air coolant stream 21B then exits from additional ports 18 carrying heat with it in the manner described with respect to some of the previous figures. Also as in previous embodiments, heat exchanger 16 is in intimate thermal contact with passively conducting member 14 and 15 which can transport heat to exchanger 16 from dissipating piezoelements 12.

Specific examples of air-moving pumps 22 for use in probe 1C include those available from Nidec Corporation (100-T Franklin Drive, Torrington, Conn. 06790) and U.S. Toyo Fan Corporation (4915 Walnut Grove Avenue, San Gabriel, Calif. 91776). These vendors offer low-profile, tube-axial continuous flow devices. These example devices are characterized by moderate pressure generation and utilization of brushless DC motors. Alternative air-moving devices suitable for use as pump 22 are available from EG&G Rotron (7 Hasbrouck Lane, Woodstock, N.Y. 12498), Micronel U.S. (1280-D Liberty Way, Vista, Calif. 92083) and Labinal Components and Systems, Inc. (2275 Stanley Avenue, Dayton, Ohio 45404). These vane-axial continuous flow devices are characterized by moderate pressure generation in the range of 1–2 inches of water pressure, 24 volt DC power sources and operation at 15k–20k RPM. For the embodiment shown in FIG. 3a, neither a tube or conduit 20 in the cable 4 nor a pressurized gas connector 19 are required.

Air-pump 22 will typically require electrical power which may be delivered via electrical wires or traces passing through cable 4 from ultrasound system 9. Alternatively, the electrical power may be delivered through separate wires not contained in cable 4. An alternative within the scope of the embodiment shown in FIG. 3a includes mounting air pump 22 and/or heat exchanger 16 on the external surface of case 2. In any event, heat exchanger 16 will always be arranged to be in intimate thermal contact with a means such as thermal member 15. In the case of external mounting of heat exchanger 16, thermal member 15 would be arranged to pass heat across the wall of case 2 with little loss. To do this, member 15 may be required to penetrate case wall 2 in a hermetic manner.

Figure 3B:
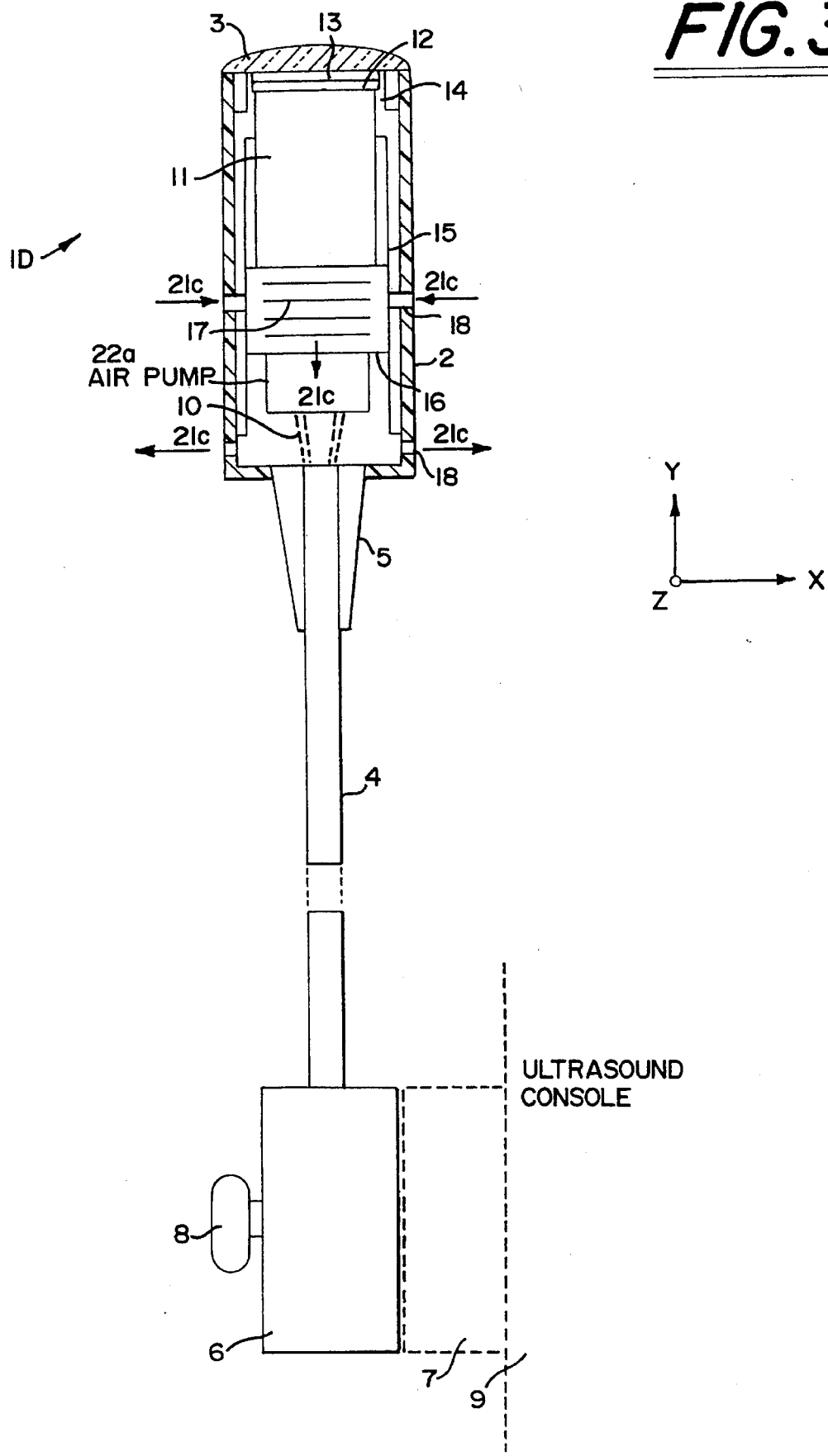
FIG. 3b is a partial cross-sectional view of a fourth embodiment, similar to the arrangement of FIG. 3a, but wherein a gaseous coolant, such as air, is drawn into the probe across the heat exchanger and then expelled from the probe through nearby probe exhaust ports.

FIG. 3b shows a fourth embodiment of the invention, similar to the embodiment of FIG. 3a, except that the coolant flow 21C is in the opposite direction. This approach may offer advantages when exhausting the coolant gas from the back (–Y end) of transducer 1D is important, to keep it away from the sonographer's hand. We stress that the ports 18 serving as exhaust ports may also be on the bottom surface (–Y end) of the transducer adjacent the strain relief 5. The intake ports 18 may be anywhere which is convenient. We also note that the air pumping or suction means 22A may be arranged to be operated in either flow direction 21C (or 21B per the previous FIG. 3a) per the user's selection. An electrical switch may be provided for this purpose.

Figure 3C:
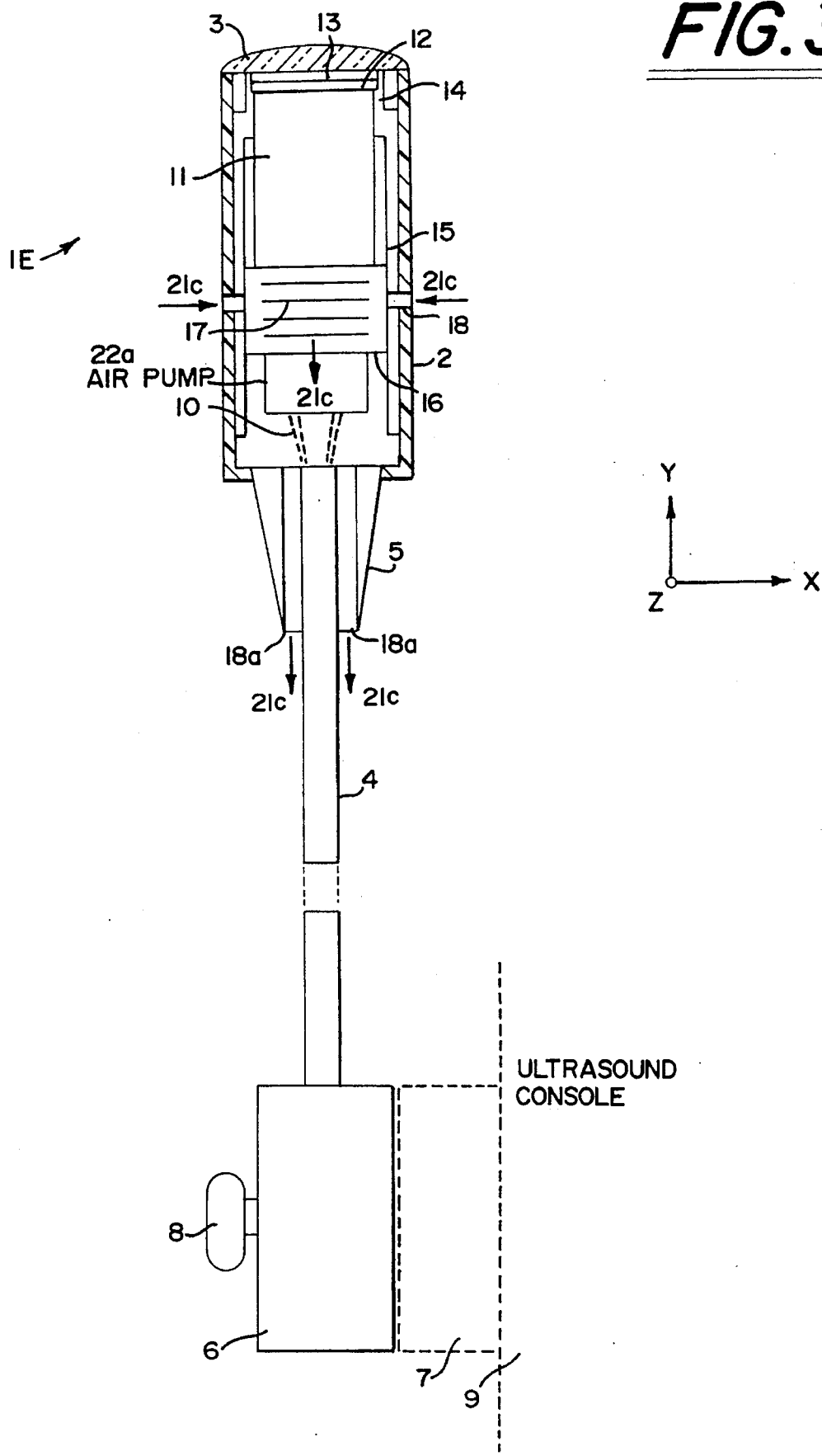
FIG. 3c is a partial cross-sectional view of a fifth embodiment, similar to the arrangements of FIGS. 3a and 3b, but wherein a coolant exhaust path is provided which ejects a gaseous coolant, such as air, from ports located comfortably away from the sonographer's hand.

FIG. 3c shows a fifth embodiment of the invention, similar to that in FIGS. 3a and 3b. Coolant flow 21C is shown entering and being drawn into probe 1E at intake ports 18 toward the heat exchanger 16, through the air pumping or suction means 22A, and subsequently exiting the probe 1E as flow 21C through internal exhaust ducts 18A inside the strain relief 5. It will be noted that the warmed exhausted coolant gas 21C is directed along the cable 4 away from the sonographer's hand. The internal detail of strain relief 5 is such that one or more gas exhaust ducts 18A are provided while maintaining some peripheral support to the cable.

The exhaust ducts 18A may be arranged to be closable or sealable, if desired, when the probe is temporarily immersed in disinfectant for cleaning. (This is true for all intake and exhaust ports for any of the embodiments.) Alternatively, one may arrange any of the disclosed designs such that ingress of disinfectant into intake and exhaust ports 18 or 18A may be tolerated, such as by ensuring the use of noncorrosive metals where disinfectant ingress takes place. It should be readily understood that one may alternatively utilize the embodiment shown in FIG. 3c with the coolant flow proceeding in the opposite direction. Miniature fans and motors which may be sterilized are commercially available, so the design challenge becomes more one of disinfecting or sterilizing, with less of a concern about damage caused by such processes.

Figure 3D:
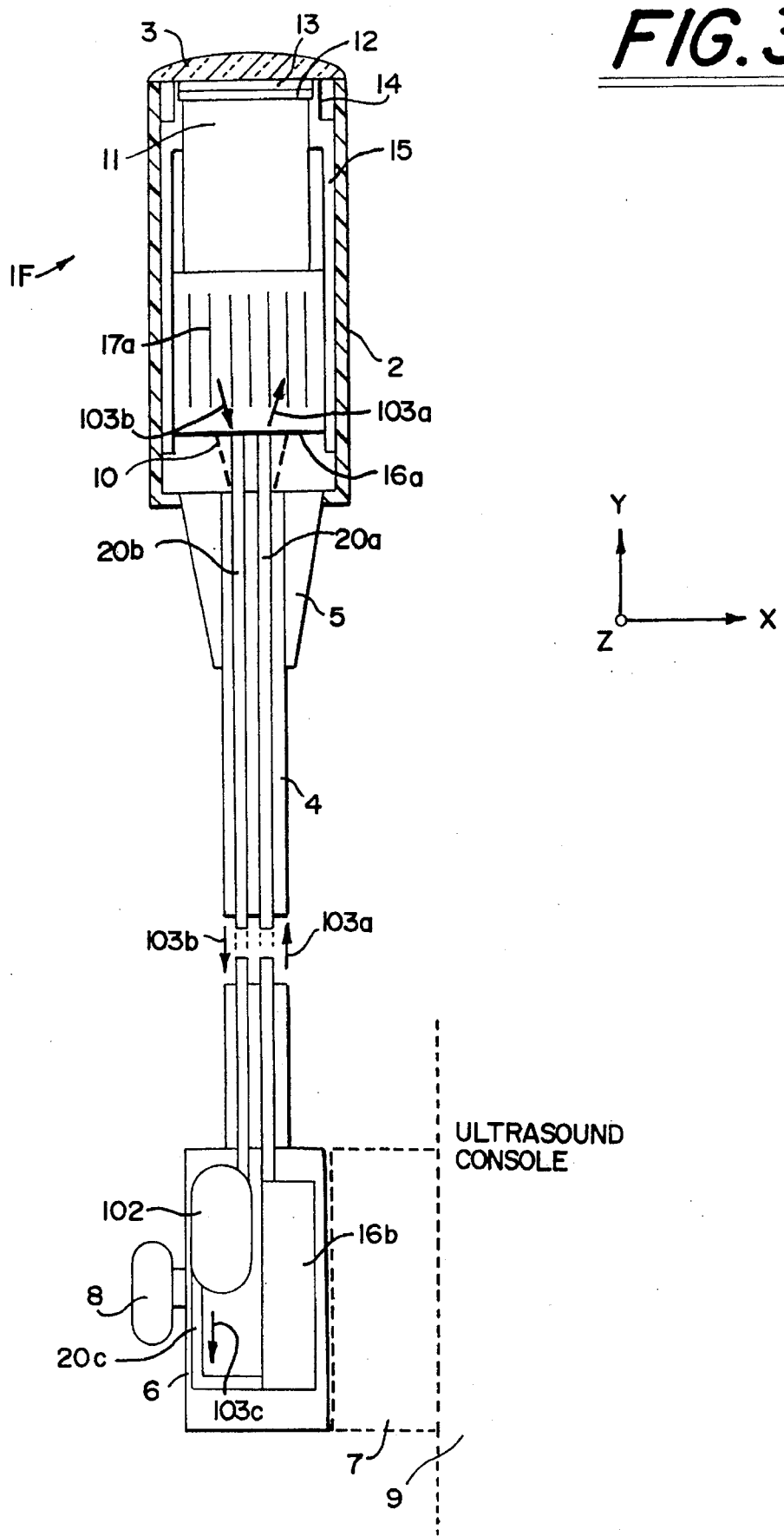
FIG. 3d is a partial cross-sectional view of a sixth embodiment wherein a closed loop cooling system is provided, utilizing either liquid, gas or other flowable coolant, wherein a probe heat exchanger passes heat into said cooling loop for transport down the cable.

FIG. 3d shows a sixth embodiment of the invention wherein a completely closed-loop cooling system is contained entirely within the probe/cable/connector assembly 1F. It will be noted that there are no coolant conduits or coolant connections made across the connector interface to the ultrasound console 9 or console connector 7. The coolant utilized may be a liquid, a liquid slurry or a gas. Most preferably, the coolant will have a liquid phase. The coolant may be a liquid, such as water or ethylene glycol, or any liquid suitably utilized in closed loop coolant systems. Precautions should be taken with any liquid used to prevent corrosion and minimize bacterial growth.

Before discussing the embodiment shown in FIG. 3d, it is important to note the technological improvements being made in research and industry in the area of recirculatable high-performance coolants. In particular, work is proceeding at labs such as the Triangle Research and Development Corporation in North Carolina on recirculatable PCM ("phase-change material") slurries containing phase change materials. The phase change ingredient within the slurry may, for example, consist of 15 micron diameter phenolic-encapsulated n-eicosane particles which are carried in distilled water. This slurry or particle/water mix has a thermal capacity of about seven times that of water alone. Eicosane is a paraffin wax with a 20 carbon chain that liquifies at 36.6 degrees centigrade.

Referring to FIG. 3d, a heat exchanger 16A is provided internal to case 2 to transport heat from the transducer components such as 14 and 15 into the heat exchanger 16A. Coolant input tube 20A passes an inflow of coolant 103A into the heat exchanger 16A and across the fins 17A of heat exchanger 16A. The coolant, after picking up heat from the fins 17A, passes out of the heat exchanger 16A in the form of outflow 103B into a second tube 20B. It will be noted that tubes 20A and 20B are shown running the length of the transducer cable 4 back to probe connector 6. Thus, cable 4 might be of a somewhat larger diameter than in previous embodiments as it now contains two coolant tubes. Exchanger 16A contains internal ducting (not shown) and/or manifolds which are necessary to distribute and route the coolant over fins of the type 17A in the most efficient manner. For simplicity, arrows schematically indicate incoming (103A) and outgoing (103B) coolant flows. It should also be understood that it is desirable that tubes 20A and 20B (within cable 4) are thermally decoupled from each other such that the coolant inflow 103A is not undesirably preheated by exiting coolant outflow 103B.

Connector 6 includes, in addition to the expected electrical interconnection means (not shown), a coolant pump 102 and a second heat exchanger 16B. A segment of tubing 20C connects pump 102 to the heat exchanger 16B such that the coolant may flow from pump 102 to the exchanger 16B in the form of coolant flow 103C as shown. Given that this is a closed loop system the coolant flow rates in the indicated flows 103A, 103B and 103C are essentially all equal. As pump 102 operates, it causes coolant to flow through the heat exchanger 16B, along tube 20A, through exchanger 16A in probe case 2, back through tube 20B and finally back to pump 102 for another cycle (or, optionally, in the opposite direction). Pump 102 may be powered electrically, mechanically or pneumatically. In the case of electrical powering, it may receive its electrical energy from the system console 9 via one or more electrical contacts in connectors 6 and 7.

Heat exchanger 16B is preferably a liquid-to-air heat exchanger. That is, liquid to be cooled is flowed inside of exchanger 16B and air on the outside of exchanger 16B, which is either naturally convected or forced across exchanger 16B, carries the heat away. Exchanger 16B may consist of a radiator (shown) or a fan and a radiator combination (not shown), for example. In an alternative approach, both a fan (not shown) and pump 102 (shown) would receive electrical power from the console 9 through the connectors 6 and 7. Sources for fans and pumps suitable for use in accordance with the embodiment of FIG. 3d have been previously described. It will be obvious to the reader that one may also arrange return tube 20B in the cable 4 such that its contained returning coolant 103B may easily pass its heat to the atmosphere via natural free convection from the surface of cable 4. In general, cable 4 is quite long and substantial cable surface area is available to do this. If the return tube 20B is arranged in the cable 4 to be near its surface and a metallic shroud is provided near the outside surface of cable 4 which is in thermal communication with tube 20B (which shroud may double as an electromagnetic shield) the return tube 20B may pass its heat to the metallic shroud such that the surface (or subsurface) of the cable 4 is warmed and made to act as a radiator itself.

It should be remembered that unlike Martin, et al., in the present embodiments there is an enormous advantage of being able to carry large amounts of heat well into the cable's length through the flowing warm coolant liquid 103B. In the case wherein cable 4 sheds the desired quantity of heat, heat exchanger 16B (and, if desired, an accompanying fan (not shown)) in the connector 6 may become unnecessary. However pump 102 is beneficially used in all cases, as natural convection circulation of the liquid will only provide a much-reduced and orientation-varying heat removal capacity from exchanger 16A. We have not shown other optional items such as monitoring thermocouples, fluid reservoirs, bubble removal traps, fill ports, flush ports or expansion means and these can be added in any desired manner as needed while not departing from the basic system shown. A feedback loop may further be included in this (or any other) embodiment of the invention, wherein a temperature sensing function triggers variations in the degree of the coolant system's operational capacity in order to control (by maintaining, rising above or dropping below) particular temperature set points. Specifically referring to FIG. 3d, it should be readily understood that one may vary the speed of pump 102 or the speed of a fan associated with heat exchanger 16B (not shown), for example, to control temperature at a desired level.

As with previous embodiments, tubing 20A and 20B may be flexible, unreinforced or reinforced, polymer tubing such as polyimide tubing. Tubing 20C in connector 6 may be rigid as it does not have to flex with the cable. Portions of the tubing in probe case 2 may also be chosen to be rigid. It should also be emphasized that the direction of the flow may be opposite that which is depicted in FIG. 3d and the order of appearance of components 102 and 16B as the coolant flows through them may be changed as desired. (For example, the pump 102 might be downstream of the exchanger 16B.)

As with previous embodiments, one may alternatively choose to implement a cooling system wherein components such as pump 102 and heat exchanger 16B are located external to the cable/connector 4/6. One may also choose to provide a separate liquid loop for the purposes of accepting heat from the probe cooling loop and, in particular, from exchanger 16B.

Figure 3E:
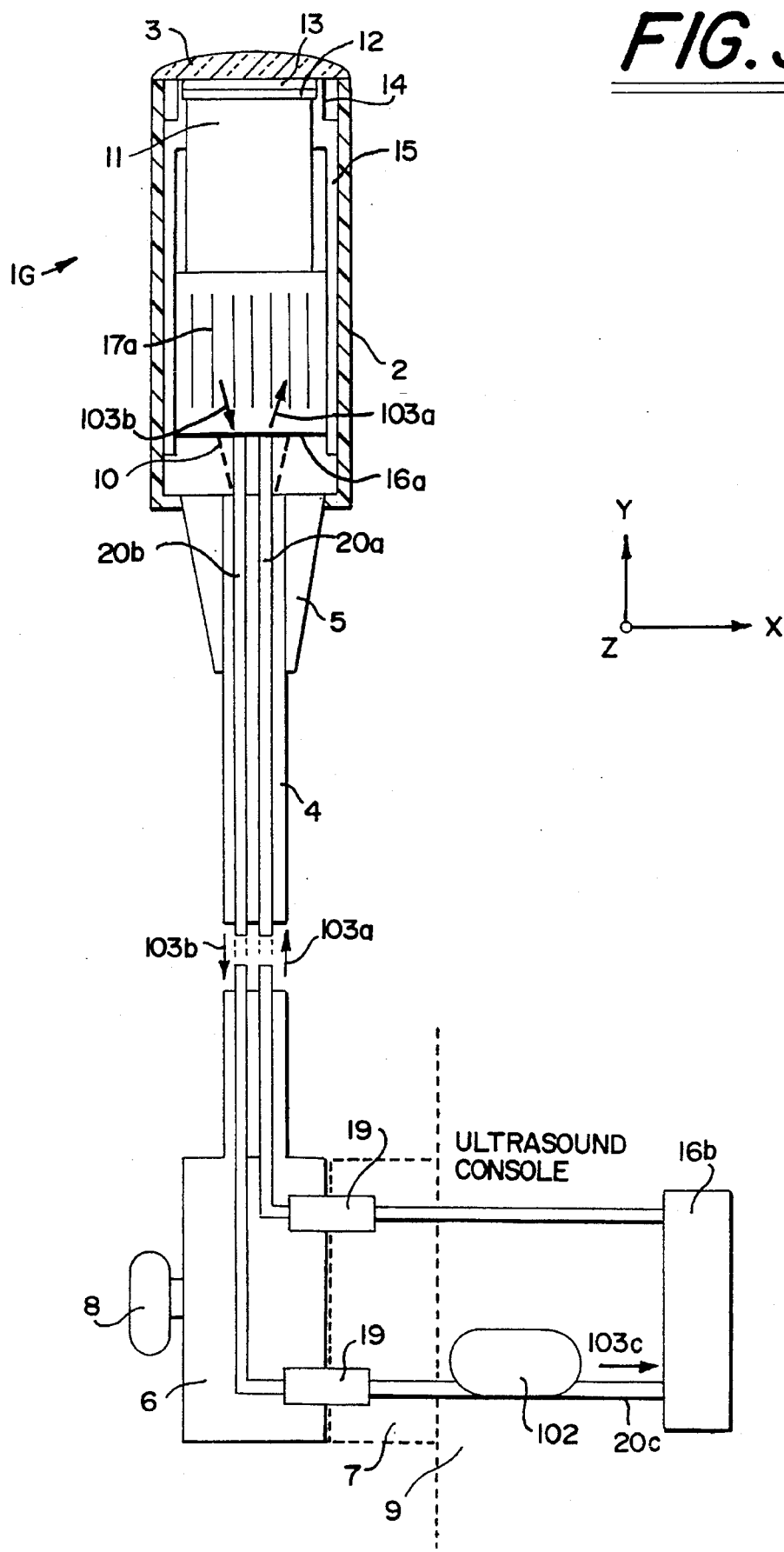
FIG. 3e is a partial cross-sectional view of a seventh embodiment similar to that of FIG. 3d, wherein the closed coolant loop passes into the system console through the connector interface.

FIG. 3e shows a seventh embodiment of the invention which is similar in construction to the embodiment shown in FIG. 3d. In this embodiment, pump 102 and heat exchanger 16B are located in ultrasound system console 9 (shown) or, alternatively, in console connector 7 (not shown). In order to implement the closed loop cooling system in this manner one may provide coolant couplings or connectors 19 in mating probe and console connectors 6 and 7 as shown. Structurally, connectors 6 and 7 may incorporate both the electrical connections (such as for interconnects 10) and coolant connectors 19. One may alternatively choose to use non-integrated, independent connectors for the electrical connectors 6 and 7 and the coolant connections 19 (not shown).

FIG. 3e shows pump 102 resident in console 9 along with the heat exchanger 16B. The tube connecting pump 102 and the heat exchanger 16B is again indicated as tube 20C having an internal coolant flow into exchanger 16B indicated again as 103C. Again the coolant flow rates of depicted flows 103A, 103B and 103C would typically be equal.

Advantages of the design of FIG. 3e are that one may use a larger and more powerful pump 102 and/or heat exchanger 16B. Heat exchanger 16B may again be accompanied by a fan (not shown) in the console 9. In the case wherein heat exchanger 16B is a liquid-to-liquid heat exchanger, console 9 would contain the other independent coolant loop (not shown). A liquid-to-liquid exchanger generally has a much higher capacity than a liquid-to-air exchanger of the same size.

Placing pump 102 and heat exchanger 16B in the console reduces the cost of the transducer significantly at the expense of requiring the use of separable coolant connectors 19. An alternative contemplated within the scope of the invention is the design of FIG. 3e wherein, in order to avoid coolant spillage, one arranges the coolant such that, when the transducer 1G is not plugged in, there is no coolant at connectors 19. In this manner, plugging and unplugging connectors 6 and 7 (and therefore connectors 19) will not result in any spillage of coolant. Once the transducer is plugged in, console 9 may cause the coolant system to eliminate all air in the coolant path as by venting.

The embodiments shown in FIGS. 3d and 3e could utilize a liquid or liquid phase-change coolant, or even a gas coolant.

Figure 4:
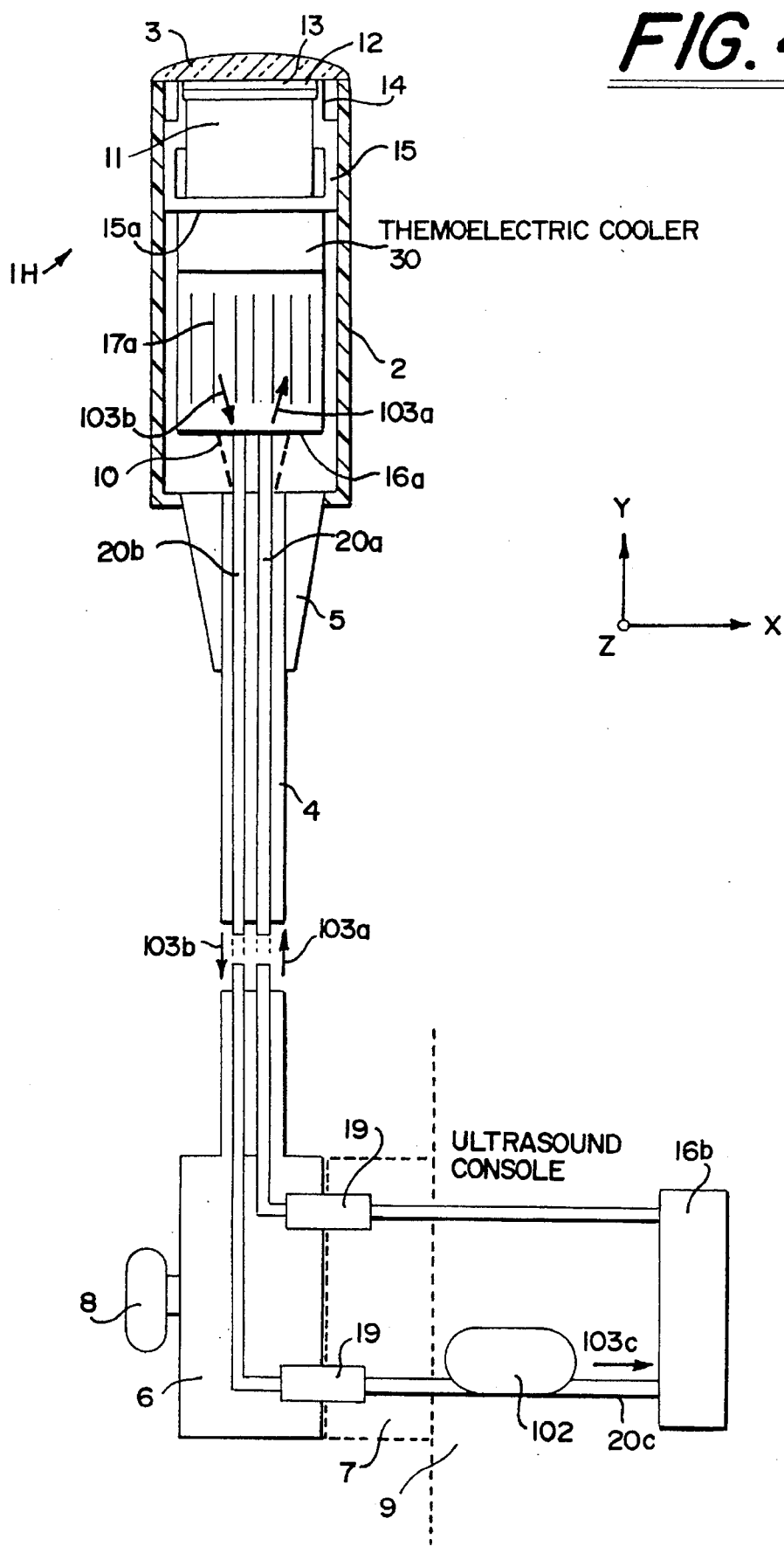
FIG. 4 is a partial cross-sectional view of an eighth embodiment wherein a thermoelectric cooling device is thermally coupled to the heat dissipating piezoelements and their local associated passive heat dissipating members.

FIG. 4 shows an eighth embodiment of the invention. FIG. 4 depicts a system similar to that of FIG. 3e but with a thermoelectric cooling device 30 in the thermal path between passive conducting members 15, 15A and heat exchanger 16A. Note that the thermal member 15A extends beneath acoustic backer 11 such that heat may be deposited in the top cooling surface (+Y surface) of thermoelectric cooler 30. Cooler 30 would typically consist of an electrically powered junction device capable of establishing a thermal gradient and transporting heat through its thickness along the Y axis (sometimes referred to as a Peltier device). Such devices, although capable of moving appreciable quantities of heat, are typically rather inefficient. Thus, the cooling system components described with respect to the embodiment shown in FIG. 3e are available to carry away not only the piezoelement heat pumped by cooler 30, but also the waste heat generated by the cooler 30 itself. Specifically, such thermoelectric coolers 30 are available, for example, from Marlow Industries, Inc. (10451 Vista Park Road, Dallas, Tex. 75238) with heat removal capacities covering the range from 1 to 150 watts. The cold (cooling) side of cooler 30 may, depending on the heat load and specific type of cooler, have the capacity to subcool between 10 and 100 degrees centigrade. Use of a thermoelectric cooler 30 offers advantages of dynamic realtime temperature control of the transducer piezoelements and/or the thermal capacity to actually subcool the piezoelements 12 as described without requiring a conventional freon-style refrigeration system. The reader will realize that the thermoelectric cooler 30 may be arranged to dump its heat to any of the other thermal means of the system embodiments described herein.

A specific advantage of a thermoelectric cooler 30 is appreciated when performing high frequency ultrasound imaging of near-surface tissues. In these growing applications, increasing amounts of heat energy are being generated in the probe and in the tissue as manufacturers attempt to achieve the highest possible resolution at the maximum allowable acoustic intensities. It would be rather difficult to maintain a reasonable lens temperature unless a cooling device 30 having very large cooling capacity (a device capable of subcooling may serve this purpose) is present in close proximity to the piezoelements, lens and tissue.

Figure 5:
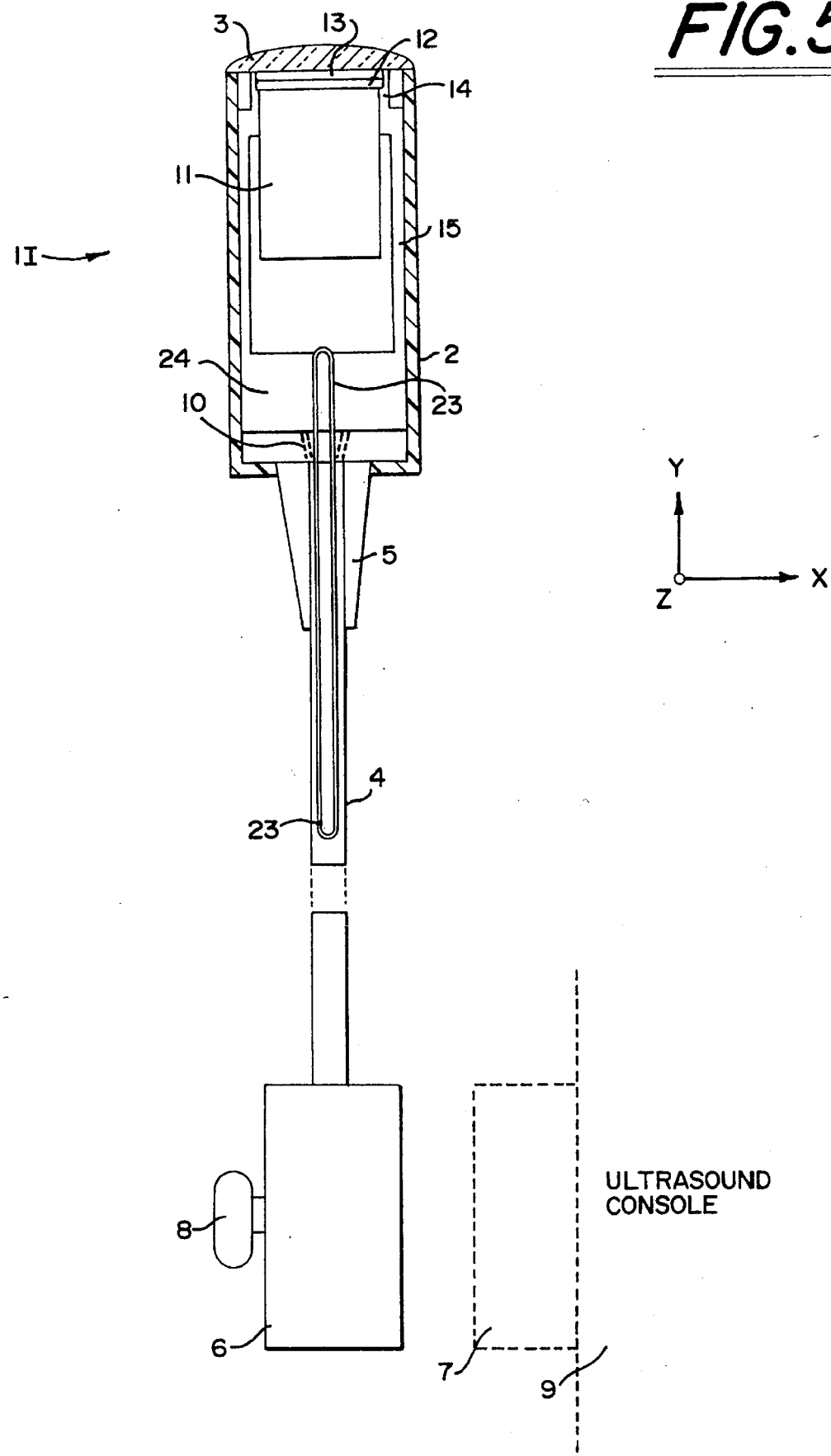
FIG. 5 is a partial cross-sectional view of a ninth embodiment of a device in accordance with the invention wherein a flexible and generally tubular heatpipe is utilized as the active cooling component.

FIG. 5 depicts a ninth embodiment of the invention. In the design shown in FIG. 5, a flexible tubular heat pipe 23 is thermally connected via thermally conductive member 24 to the previously described thermal member 15. Heat pipe 23 extends into cable 4 for a fair length, perhaps a foot or more, and is thermally coupled to the outer jacket of cable 4 within such length. We have previously described recent efforts at designing conductive members which pass into cable 4 from the interior of case 2, and internal thermal members such as 15 and 14. Those familiar with the heat pipe art will recognize that because heat pipes can carry far more heat than an equivalent cross-section of solid copper, considerable thermal conduction is achieved along the cable with a rather small diameter heat pipe 23. Heatpipe 23 may also be very flexible. Thus, heat energy which is conducted into the end of the heatpipe 23 positioned in case 2 via thermally conducting members 14,15 and 24 causes the internal evaporation of the working fluid of heatpipe 23 and its subsequent recondensation in the heat pipe's cooler regions further along the cable. Due to the superb axial heat carrying performance of heatpipes, this phase change is done with a very small temperature gradient. Thus, the full benefit of the additional cable area's ability to convect heat passively is effectively realized. Those skilled in the art of heatpipes will be aware that one frequently utilizes fluid reservoirs and pressure-compensating bellows with heatpipes and that such related means may easily be incorporated in case 2.

A significant advantage of the device of FIG. 5 is that a very substantial increment is made in thermal dissipation performance using a semiactive heatpipe (semiactive in that the gas vapor moves but no power is required to operate it). Because no power is used to operate this cooling means then there is no concern about vibration or electrical noise generated by any active pumping or suction means such as pump 22. As for previous heat removal means, heatpipe 23 may be external to the cable in some cases. For example, one may have an optionally employed heatpipe 23 which plugs into a thermally conductive "jack" in the case. Such an external heatpipe 23 could be draped to the side of the probe during use. Such an external pipe could also have an attached radiator surface, for example. Means could be provided for such an optional heatpipe to alert the ultrasound system that the external heatpipe means is plugged in and that higher acoustic power levels are allowable without fear of thermal problems. Heatpipe 23 may also extend all the way back to connector 6 in cable 4.

Heatpipe 23 may be a classic heatpipe in that it uses an internal wick structure to return the coolant fluid to the hot spot after the coolant vapor recondenses to said fluid phase in the cooler region of said heatpipe 23. However, systems suitable for use as heatpipe 23 include evaporation/condensation systems not necessarily involving a wick structure dedicated to capillary pumping of recondensed coolant back to the heat source. Specifically, a system called the Oasis™ system produced by Aavid Engineering consists of an evaporator (which is thermally coupled to the user's device to be cooled) and a separate condenser panel. The evaporator is connected to the condenser by two tubes. In a manner similar to the heat pipe, the evaporator generates a liquid vapor in response to the heat input. The heated vapor flows through one of the tubes to recondense back into the liquid phase in the condenser panel. The recondensed fluid in the condenser panel is returned to the evaporator through the second tube in liquid form. This system utilizes Fluorinert™ fluid which has a boiling point of 57 degrees centigrade. Thus, the evaporator never gets hotter than 57 degrees centigrade because a phase change from liquid to vapor takes place at that temperature. It will be recognized that the main difference between this and the classic heatpipe is that liquid is flowing in a tube rather than the liquid flowing via capillary action through a porous wick on the inner surface of the walls of a tube. Using the Aavid system, one may depend on free convection cooling of the condenser or may alternatively utilize forced convection cooling of said condenser. The potential disadvantage of the Aavid device is that the transducer probe 1I may be oriented at an unpredictable angle and/or held at an unpredictable height. One may thus have problems with the liquid in the tubes not flowing properly. In a classic heatpipe design with a wick structure inside heatpipe 23, the capillary wick keeps working regardless of the probe's position or orientation.

Figure 6:
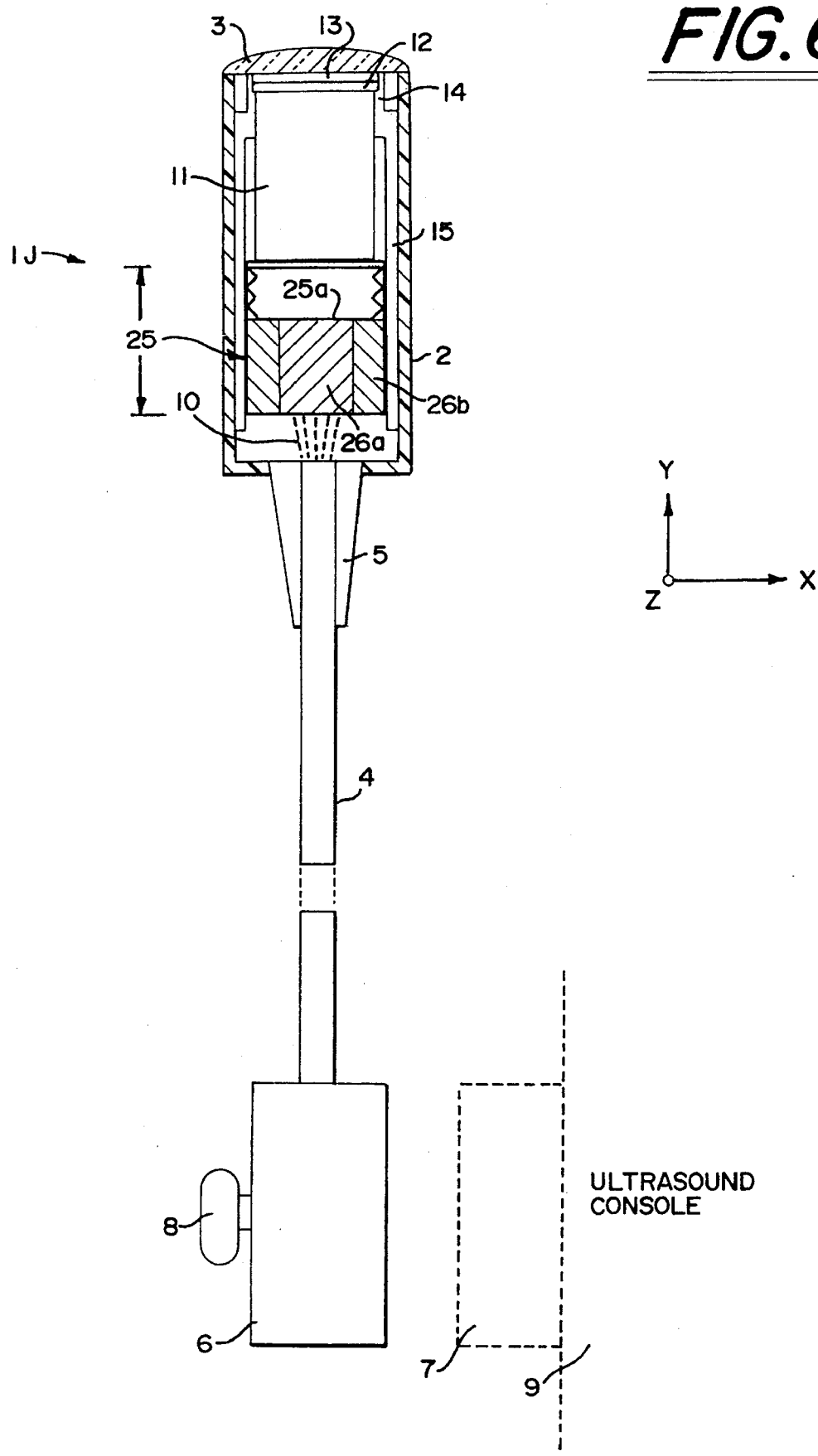
FIG. 6 is a partial cross-sectional view of a tenth embodiment of the device in accordance with the invention wherein a material having a large phase-change heat absorbing capacity is placed in the probe and thermally coupled to the dissipating device.

FIG. 6 shows a tenth embodiment of the invention. A container 25 is provided in case 2 in intimate thermal contact with thermal members 15. Within the container 25, which would typically be fabricated of a thermally conducting metal, an optional movable preloaded diaphragm 25A is shown which is slidable in the +Y direction and capable of applying modest downward (−Y direction) pressure. Adjacent to and in contact with slidable diaphragm 25A is a phase-change material which is depicted in both of its operational forms 26A and 26B. The phase-change material is a material which absorbs a very large amount of heat when its phase changes from one phase to the other. For example, H₂O takes the form of water and ice at 0 degrees centigrade and to totally convert from one form (phase) to the other for a given quantity of H₂O requires a considerable flow of thermal energy. This flow of energy does nothing to change the temperature of the water/ice mixture from 0 degrees centigrade while this phase-change is taking place. Thus one's drink can be kept cold as long as ice is present. This property of absorbing a large quantity of thermal energy without changing temperature can be very useful if the temperature in question is of technical use.

In probe 1J, if a phase-change material is chosen whose phase-change takes place at a warm but tolerable temperature to the patient and sonographer, then the phase change material may absorb a substantial quantity of heat without changing temperature (getting any hotter) and without the need to pass the heat to the environment immediately. For short-term thermal dissipations by piezoelements 12, the phase change material will absorb the waste heat and keep the probe at the acceptable phase-change temperature. The phase change material is therein acting essentially as a thermal capacitor which is either charging (absorbing heat) or discharging (dumping previously absorbed heat). Within container 25 can be seen the two phases of the phase change material, namely phases 26A and 26B. As depicted, phase 26B may, for example, be a molten phase and phase 26A a solid phase.

Probe 1J is depicted at a moment in time when the phase-change material is partially converted from one phase to another. In this specific example, waste heat is flowing down thermal member 15 and into the left and right sides of container 25 whereupon the heat causes the molten phase 26B to first form adjacent to each thermal plate 15. Since not enough heat has yet flowed into the container 25 there is still a region in the middle of the container 25 where the solid phase 26A of the phase-change material is still present. At a later point in time, assuming heat input continues into container 25, the remaining region of solid phase-change material 26A in that central portion of container 25 would also become molten. At that point the container 25 and its contents can no longer absorb heat at the constant phase-change temperature and further heat input will only result in the container 25 and probe 15 getting hotter.

The slidable pressurizing diaphragm 25A applies a constant pressure for the purpose of urging the phase-change material to remain in contact with the internal walls of container 25 as the phases change back and forth. This is necessary because many phase-change systems are accompanied by small but not insignificant volume changes. One example of a phase change material useful for container 25 would be a wax-like substance having a deformable waxy solid phase and a liquid phase. Slidable diaphragm 25A could keep the two phases of such a wax-based system from growing voids or air pockets during phase changes due to volume changes. Specific phase change materials for use in the FIG. 6 system include the series of paraffin waxes of which eicosane is one. Paraffin waxes with hydrocarbon chains of between about 18 (octadecane) and 22 carbon atoms have melting points between 25 and 41 degrees centigrade. Specifically, octadecane has a melting point of 28.1 degrees centigrade and a heat of fusion of 58.2 calories per gram. Eicosane (20 carbons) melts at 36.6 degrees centigrade and has a heat of fusion of 59.1 calories per gram. These two materials experience only about a 7% density change during melting and freezing thus the concern about volume changes may be minimized.

Other phase change material systems may be considered for use in probe 1J. Some of these undergo sublimation/ evaporation. Other heat-of-fusion, phase-change material systems include hydrated inorganic salts (e.g. zinc nitrate which melts at 36.2° C. and has a heat of fusion of 31 cal/gm), anhydrous inorganic salts (e.g. metaphosphoric acid HPO4 with specs of 42.5° C. and 25 cal/gm) and compounds such as Glauber's salt ($Na_2SO_4.10H_2O$ which changes phase at 32.2° C.). The wax systems are preferred because there is minimum chance of phase separation. Indeed, tests have been reported wherein the above wax materials have been phase-cycled as many as 30,000 times without any change in thermal capacity.

Note that there is an upper thermal capacity limit of the container 25 phase-change heat-accumulation device. Once it is filled with heat (the beneficial phase change has run its course), its heat absorption characteristics are no longer beneficial in probe 1J. However, in typical operation of transducer devices, there are frequent occasions when short-duration excessive heatflow is generated. In such cases, container 25 may be beneficial as a thermal reservoir. During other portions of the probe's operation, when heat flow is more typically at a lower level, other cooling means of the probe (such as the prior art passive convection means) may be utilized to gradually allow the material in phase 26B to revert back to the solid phase 26A, as well as to cool the probe in the normal manner. In an extreme case, one may operate the probe in a very high power mode, a mode which cannot practically be cooled in real time even by aforementioned air pressurization or suction means, wherein most or all of the excessive heat is dumped into the phase change material. As long as this process is finished before the phase change completely converts, there is no heating problem other than providing a sufficient wait for normal cooling means to induce reversion of the phase change material back to the original phase before the probe can be used in the excessive power mode again.

Hyperthermia, the use of directed heat to treat or kill cancerous cells in bodily tissue, could be an obvious application of any of the means of this invention and particularly of the high-capacity phase-change and thermoelectric means possibly coupled and integrated with means such as those depicted in earlier FIGS. 2a,2b,3a,3b,3c,3d,3e and 5. For example, one would use the imaging transducer probe 1 to both image (locate and target) the cancerous regions and, when targeted, deliver intense heating ultrasound or sonic energy to the cancerous tissue within the body. The ultrasound console 9 may be arranged so that it automatically, via software, has the intelligence to keep track of the cancerous sites and their integrated thermal dosages despite some amount of unavoidable movement of the transducer. It will be recognized that the hyperthermia mode, wherein heat is purposely being acoustically generated in the patient's tissue by transducer 1, represents a very high instantaneous heat flow within the transducer as well. The high-capacity thermoelectric and phase-change components of the invention would be suitable to prevent overheating to the patient or sonographer in such instances.

A further aspect of the present invention addresses the problem of circumventing the two thermal chokepoints commonly found in transducers. These chokepoints are related to areas where heat is being generated in a concentrated manner in a small space. What is required is to spread this concentrated heat out so that it can be more easily coupled into the active thermal means of the previous figures (or into any other means including the prior art means).

As previously noted, it is difficult to get electroacoustic waste heat to flow along or parallel to the piezoelements 12 in the +−X directions into thermal members 14 and 15. Metallic electrodes positioned in at least some of the interfaces of lens 3 and matching layers 13, matching layers 13 and piezoelements 12, or piezoelements 12 and backing material 11, which are used for electrical purposes, must be kept thin enough so that they don't degrade the acoustic operation of the transducer. This greatly limits the electrode's ability to pass heat along (or parallel to) piezoelements 12. Materials used to fabricate matching layer(s) 13, piezoelements 12 and acoustic backer 11 frequently have mediocre thermal conductivity. There are a few exceptions to this general problem. As an example, carbon-based matching layers have been used which have acceptable acoustic properties, somewhat better than mediocre thermal properties, but problematic handling (very brittle) and adhesion properties. For a large aperture transducer (having a great number of elements, each of which is fairly long), the heat transmission problem is exacerbated in that the large piezoelement array is generating greater amounts of heat, and the distance from its center to its edges is even greater. This can lead to the emitting aperture having a hot spot in the middle despite the best effort to remove the heat at the edges.

Figure 7A:
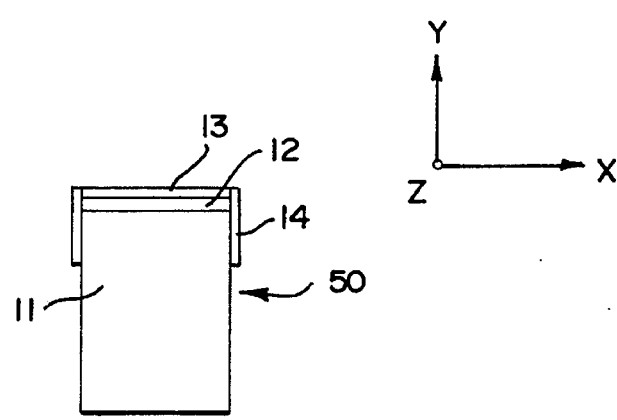
FIG. 7a is a side view of a piezoelement transducer assembly of the type used in the device shown in FIG. 1.
Figure 7B:
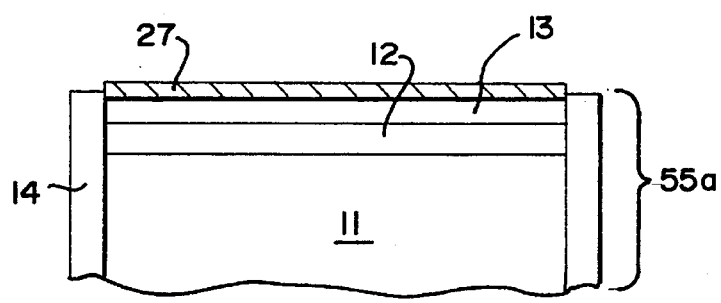
FIGS. 7b–7d are cross-sectional views of a piezoelement transducer assembly comprising further embodiments of the invention providing enhanced passive thermal means for spreading out the concentrated heat being generated in and near the piezoelements through application of thin-film diamond.
Figure 7C:
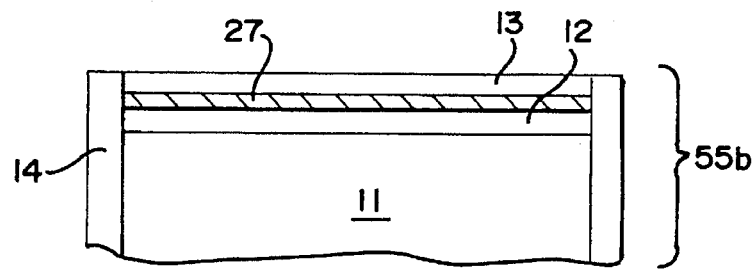
Figure 7D:
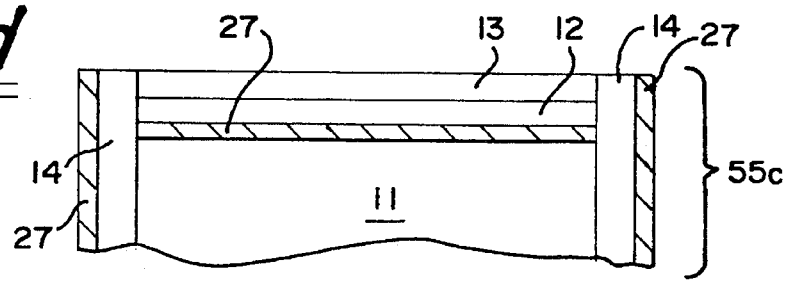

FIGS. 7b–7d show variations on an eleventh embodiment of the invention. FIG. 7a shows the electroacoustic transducer device 50 of the previously depicted probes 1A–1J consisting of acoustic backer 11, piezoelements 12, matching layer(s) 13, and passive thermal members 14 and 15 (15 not shown).

FIG. 7b is an enlarged view of transducer assembly 55A, similar to assembly 50, but with unique differences outlined below. A new material layer 27 is shown situated on top of matching layer(s)13. In FIG. 7c, in assembly 55B, layer 27 is seen therein shown situated at the interface of the matching layer(s) 13 and piezoelements 12. In FIG. 7d, in assembly 55C, material layer 27 is shown situated between the acoustic backer material 11 and piezoelements 12. In FIG. 7d, the added material 27 is also shown situated on the surface of each thermal member 14.

Material 27 is a thermal enhancement layer consisting of a film of diamond or diamond-like carbon-based material which is either deposited on one or more of the acoustic components or laminated to the acoustic components. Preformed diamond films, already deposited and formed, may be procured from companies such as Diamonex, Inc. (7150-T Windsor Drive, Allentown, Pa. 18106-9328) and Norton Company, Materials Division (1-T New Bond Street, Worcester, Mass. 01615-0008). Whether purchased as a component or deposited by the transducer builder the growth of diamond films frequently utilizes methane-based or other hydrocarbon-based plasma or arc-jet processes. Some of these processes are high temperature processes suitable only for deposition on a ceramic such as PZT, vitreous carbon or graphite and others are suitable for low temperature deposition even on plastics such as on acoustic matching layers. Diamond films or "substrate" materials typically have 4 to 7 times the thermal conductivity of copper. Thus, for a diamond film having 5 times the thermal conductivity of copper, the same net heat-carrying capacity as copper is achieved at only ⅕th the thickness of the thermally equivalent copper.

These thinner layers of diamond may thus be better tolerated in the acoustic structure and may even be utilized to serve as an acoustic component such as one of or a portion of one or more matching layers 13. If diamond film 27 is utilized on a surface to which electrical contact must be made, either the diamond film can be doped to be electrically conductive, or contact vias may be provided through the diamond film so that electrical interconnections may pass through the diamond layer(s) 27.

Other applications for diamond films 27 in the transducer to conduct heat are contemplated as being within the scope of the invention. For example, one may deposit or place diamond films between each member of the array of piezoelements 12, such as in the kerfs or gaps between each piezoelement in the X-Y plane. If this is done in a manner so as not to fuse the elements 12 together, then the elements will still be able to operate acoustically yet will have an added capacity to pass heat along their lengths (along the +−X axis) between them. Obviously any mechanical constraint the diamond film(s) present to the vibrating piezoelements 12, assuming the diamond film(s) 27 touches the elements 12, must be taken into account in the acoustic design. This is very critical for large aperture high power modes of operation wherein it is otherwise difficult to avoid creating a hot-spot in the middle of the acoustic aperture (at the element midpoints for example).

Figure 8:
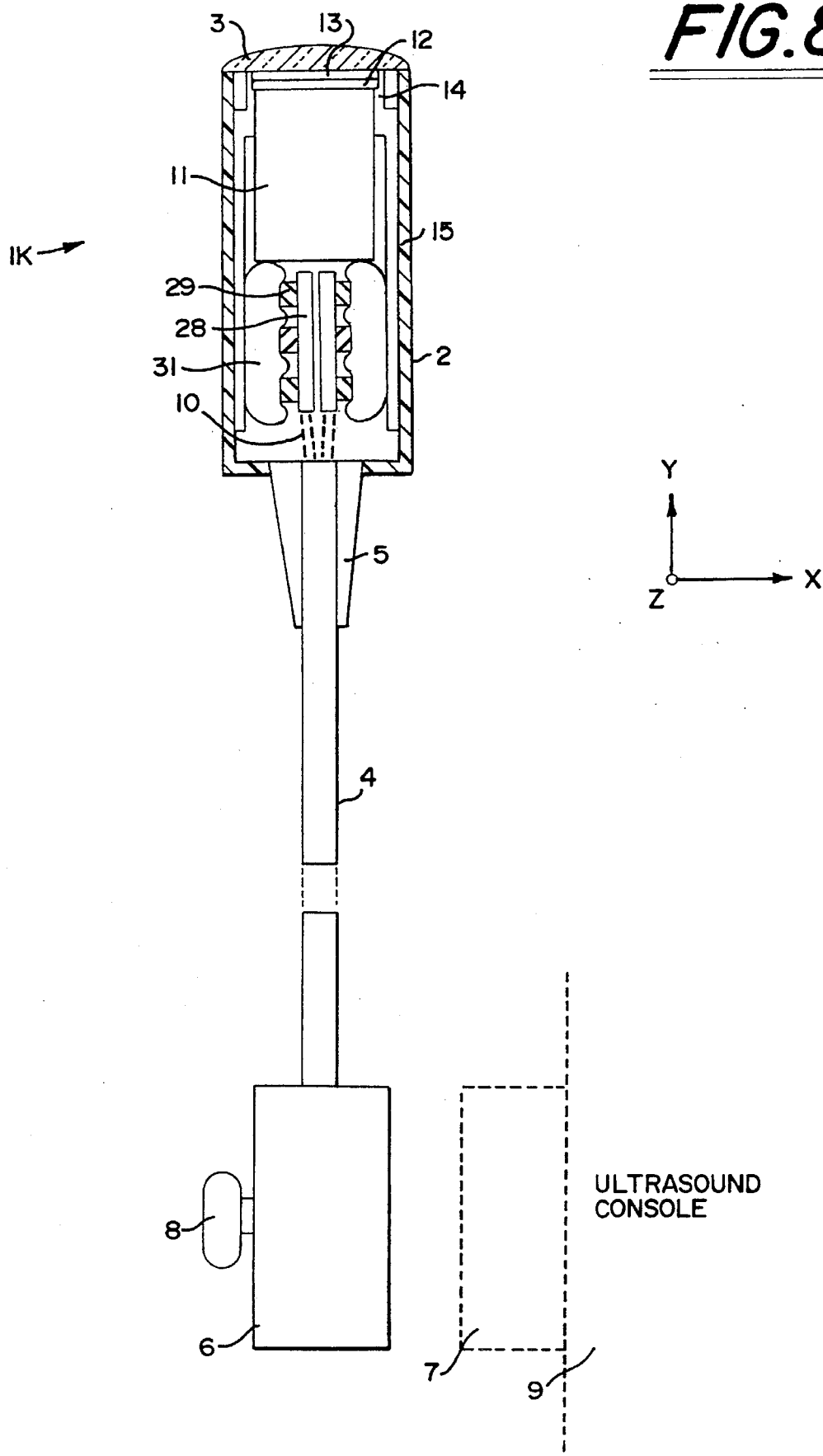
FIG. 8 is a cross-sectional view of a twelfth embodiment of the invention including cooling plates and a transducer assembly which contains supporting electronic circuitry which passively dissipates concentrated heat along with hermetically sealed liquid-filled bags which serve to transport heat across the highly irregular interfaces between the electronics and the plates.

FIG. 8 depicts a novel solution to a second thermal chokepoint of modern transducers. This improvement spreads concentrated heat into any convenient thermal sinking means, including into those of the prior art, or into any of the active means of this invention. In FIG. 8, two printed circuit boards or substrates 28, each supporting electronic components 29, are mounted back-to-back in the case 2 of transducer 1. The boards 28 and components 29 may, for example, consist of multiplexing electronics, amplifiers, matching electronics, computational and/or memory electronics or any other electronic or heat-producing subsystem used in the operation of transducer 1. Liquid-filled bags 31 are deformably squeezed between each board 28 and component 29 subsystem, and thermal member 15. Such fluid-filled and hermetically sealed deformable bags 31 may be obtained from 3M Industrial Chemical Products Division (Building 223-6S-04, 3M Center, St. Paul, Minn. 55144-1000). It will be noted that the surface of each board subsystem has an irregular surface shape due to components 29 mounted upon them and that bags 31 conform nicely to said irregular surfaces thus insuring maximal thermal contact. Bags 31 are typically metalized polymeric bags containing 3M Fluorinert™ thermally-conductive liquids. Thus, heat may freely flow out of the components 29 directly into contacting and juxtaposed bag 31, and then from bags 31 into plates 15. The great advantage of bags 31 is that one may easily disassemble board 28 and components 29 from the transducer 1K at any point in time to service the transducer without having to deal with the removal of the alternative and messy thermally-conductive potting compounds.

The many features and advantages of the present invention will be readily apparent to one of average skill in the art. Numerous modifications to each of the embodiments discussed herein are anticipated as being within the scope of the invention. It is anticipated that the use of the active, semi-active and passive thermal solutions described herein, as well as combinations of the particular solutions described herein, and combinations of these solutions herein with the prior-art solutions are within the scope of the invention. It is also anticipated that uses in cases wherein the ultrasound transducer is part of a medical device supporting other medical functions as for the increasingly popular ultrasound/optical imaging probe instruments are within the scope of the invention. In these cases, the thermal control means of this invention may also support the thermal control of the other device, such as the optical illumination/imaging means in our above example.

One skilled in the art will recognize the beneficial application of the invention to ultrasound probes other than the flat phased-arrays depicted in the figures. As examples, one may beneficially apply the invention to curved phased arrays, two-dimensional phased arrays, annular mechanically-scanned ultrasound transducers, or to single or multi-element catheter-based imaging or doppler transducers.

What is claimed is:

1. An ultrasound transducer assembly, comprising:
   a housing;
   a transducer mounted in the housing, the transducer operable to transmit ultrasonic energy along a path; and
   active cooling means positioned outside of the path and in thermal communication with the transducer for actively removing heat generated by the transducer by active thermal transport of heat energy from the transducer.

2. The transducer assembly of claim 1 wherein the active cooling means is a heat exchanger including a flowed coolant passing through at least a portion of the heat exchanger.

3. The transducer assembly of claim 2 wherein the coolant is a liquid.

4. The transducer assembly of claim 3 wherein the coolant is primarily composed of water.

5. The transducer assembly of claim 3 wherein the coolant contains a phase change constituent.

6. The transducer assembly of claim 2 wherein the coolant is a gas.

7. The transducer assembly of claim 2 wherein the coolant is primarily air.

8. The transducer assembly of claim 2 wherein the assembly is designed to be mated with control electronics positioned in a console, and wherein the assembly further includes a cable and cable connector, the cable and cable connector including at least an electrical coupling connected to the transducer and the control electronics.

9. The transducer assembly of claim 8 wherein the coolant is circulated through the heat exchanger by a pump located in the housing.

10. The transducer assembly of claim 8 wherein the cable further includes a coolant conduit, and the coolant is circulated through the cable and the heat exchanger by a pump located in the cable connector.

11. The transducer assembly of claim 8 wherein the cable further includes a coolant conduit, the cable connector includes a coolant conduit, the console includes a mating connector for coupling with the cable connector, the mating connector including at least an electrical coupling, and coolant is circulated through the cable, console connector, mating connector and heat exchanger by a pump located in the mating connector.

12. The transducer assembly of claim 8 wherein the cable further includes a coolant conduit, the cable connector includes a coolant conduit, the console includes a mating connector for coupling with the cable connector, the mating connector including at least an electrical coupling and a coolant conduit, and the coolant is circulated through the cable, cable connector and mating connector by a pump located in the console.

13. The transducer assembly of claim 8 further including a multi-pass, closed loop coolant path coupled to the heat exchanger.

14. The transducer assembly of claim 13 further including a second heat exchanger coupled to the closed loop coolant path.

15. The transducer assembly of claim 14 wherein the cable includes a portion of the closed loop coolant path, the second heat exchanger is positioned in the cable connector, and coolant is circulated between the heat exchangers through the cable.

16. The transducer assembly of claim 14 wherein the cable includes a portion of the closed loop coolant path, the second heat exchanger is positioned in the mating connector, and coolant is circulated between the heat exchangers through the cable.

17. The transducer assembly of claim 14 wherein the cable includes a portion of the closed loop coolant path, the second heat exchanger is positioned in the console, and coolant is circulated between the heat exchangers through the cable, the cable connector and the mating connector.

18. The transducer assembly of claim 2 wherein the flowed coolant is included in a single pass coolant path coupled to the heat exchanger.

19. The transducer assembly of claim 2 further including a multi-pass, closed loop coolant path coupled to the heat exchanger.

20. The transducer assembly of claim 2 wherein the active cooling means is a closed loop, multi-pass coolant system coupled to a heat exchanger.

21. The transducer assembly of claim 2 wherein the active cooling means is a single pass system coupled to a heat exchanger.

22. The transducer assembly of claim 1 wherein the active cooling means comprises a heat pipe.

23. The transducer assembly of claim 22 wherein the transducer assembly is controlled by control electronics positioned in a console, wherein the assembly further includes a cable and cable connector for electronically coupling the transducer with the control electronics, and wherein a first portion of the heat pipe is thermally coupled to the transducer, to accept heat from the transducer, and a second portion of the heat pipe is positioned in the cable such that heat generated by the transducer is carried into the cable.

24. The transducer assembly of claim 23 wherein the heat pipe includes a control bellow.

25. The transducer assembly of claim 23 wherein the heat pipe includes a working fluid reservoir.

26. The transducer assembly of claim 23 wherein the cable and heat pipe are flexible.

27. The transducer assembly of claim 1 wherein the active cooling means comprises an evaporator assembly and a condenser, wherein the evaporator is thermally coupled to the transducer.

28. The transducer assembly of claim 27 wherein the condenser and the evaporator are coupled by at least one coolant conduit for transport of evaporated or condensed coolant liquid.

29. The transducer assembly of claim 1 wherein the active cooling means is a thermo-electric cooler.

30. The transducer assembly of claim 29 wherein the thermoelectric cooler is positioned within the housing and is thermally coupled to the transducer.

31. The transducer assembly of claim 29 wherein the thermoelectric cooler has a thermal capacity range sufficient to cool the transducer below ambient temperature when the transducer is operating.

32. The transducer assembly of claim 1 wherein the active cooling means utilizes a phase change material.

33. The transducer assembly of claim 32 wherein the phase change material has a finite capacity to absorb heat, said finite capacity being limited by the phase change taking place in all available phase-change material at a substantially constant temperature during said heat flow.

34. The transducer assembly of claim 33 wherein the phase change material is provided in at least one deformable container.

35. The transducer assembly of claim 33 further including a container defined by a pressurizing member in contact with the phase change material.

36. The transducer assembly of claim 33 wherein the phase change material is provided within the housing.

37. The transducer assembly of claim 33 wherein the phase change material has a first operational phase comprising a liquid and a second operational phase comprising a solid.

38. The transducer array of claim 32 wherein the flowed coolant consists of, at least in part, a phase change material in a liquid.

39. The transducer assembly of claim 32 wherein the phase change material is a paraffin wax.

40. The transducer assembly of claim 39 wherein the paraffin wax is eicosane.

41. The transducer assembly of claim 1 wherein the transducer includes a layer of diamond or diamond-like carbon.

42. The transducer assembly of claim 41 wherein the diamond or diamond-like carbon is applied to one or more surfaces of the transducer.

43. The transducer assembly of claim 41 wherein the diamond or diamond-like carbon comprises a preformed substrate which is bonded to a portion of the transducer.

44. The transducer assembly of claim 1 further including a passive cooling assembly in thermal contact with the transducer and the active cooling means.

45. The transducer assembly of claim 44 wherein the passive cooling means includes a layer of diamond or diamond-like carbon.

46. The transducer assembly of claim 44 wherein the transducer further includes a diamond or diamond-like carbon layer in contact with the passive thermal member.

47. The transducer assembly of claim 46 further including transducer electronics mounted in the housing and a phase change material provided in a deformable bag mounted between the transducer electronics and at least one passive thermal member.

48. The transducer assembly of claim 1 further including a liquid heat-transfer fluid contained within a closed deformable container, the closed deformable container being located within the housing and outside of the path such that the fluid is allowed to make thermal contact, through the deformable container, with smooth or irregular surfaces in the housing.

49. The transducer assembly of claim 48 wherein the fluid is a fluorinated liquid.

50. The transducer assembly of claim 48 wherein transducer electronics are provided as components on a printed circuit board situated in the housing, and wherein the closed deformable container is positioned between the components and a passive thermal heat sink in the housing.

51. A transducer assembly, comprising:
   a housing;
   a transducer mounted within the housing, the transducer operable to transmit ultrasonic energy along a path;
   a heat exchanger thermally coupled to the transducer, said coupling consisting of a passive thermally conductive assembly; and
   a flowing coolant fluid thermally coupled to the heat exchanger wherein the heat exchanger and the flowing coolant fluid are positioned outside of the path of the ultrasonic energy.

52. The transducer assembly of claim 51 wherein the flowing coolant is provided in a closed loop, recirculating coolant system coupled to the heat exchanger.

53. The transducer assembly of claim 51 wherein the flowing coolant is provided in a single pass coolant path.

54. The transducer assembly of claim 51 wherein the circulating coolant is a gas.

55. The transducer assembly of claim 51 wherein the circulating coolant is a liquid.

56. The transducer assembly of claim 51 wherein the housing includes a plurality of input and output apertures, and wherein the coolant is directed into and out of the housing through the apertures by a pump mounted in the housing.

57. The transducer assembly of claim 51 wherein the housing includes a plurality of input and output apertures, the transducer is arranged to be coupled to a control console, and the coolant is directed into and out of the housing through the apertures by a pump mounted in the console.

58. A transducer system, adapted for use with a control console having a console connector, comprising:

a housing;

a transducer mounted within the housing;

a heat exchanger thermally coupled to the transducer;

a circulating coolant fluid thermally coupled to the heat exchanger;

a cable coupled to the housing;

a cable connector coupled to the cable, the cable connector including an electrical connector and being adapted to couple with a console connector; and a second heat exchanger, coupled to the circulating coolant.

59. The transducer system of claim 58 wherein the coolant path is a closed loop coolant path, and wherein the cable further includes a coolant conduit.

60. The transducer system of claim 59 wherein each of the cable connector and the console connector includes an electrical interconnect and a coolant conduit interconnect for coupling with the respective coolant or electrical interconnect on the cable or console connector.

61. The transducer system of claim 58 wherein the second heat exchanger is positioned in the cable connector.

62. The transducer system of claim 58 wherein the second heat exchanger is positioned in the console connector.

63. The transducer system of claim 58 wherein the second heat exchanger is positioned in the console.

64. A transducer assembly, adapted for use with an ultrasound control console to produce ultrasound images, comprising:

a housing;

a transducer mounted in the housing;

a transducer cable having a first portion coupled to the transducer and the housing and a second portion coupled to the console via a mating pair of connectors;

a thermal conductor coupled to the transducer and extending toward the transducer cable; and a heat pipe having a first portion thermally coupled to the thermal conductor and a second portion extending into the transducer cable thereby passing heat into the cable from the transducer during imaging.

65. A transducer assembly, adapted for use with a control assembly, comprising:

a housing;

a transducer mounted in the housing;

a connector conduit having a first portion coupled to the transducer and the housing and a second portion coupled to the control assembly; and a phase change material mounted in the housing in a pressure controlled container positioned in thermal communication with the transducer.

66. A transducer assembly, adapted for use with a control assembly, comprising:

a housing;

a transducer mounted in the housing;

a connector conduit having a first portion coupled to the transducer and the housing and a second portion coupled to the control assembly; and a thermoelectric cooler mounted in the housing in thermal contact with the transducer.

67. A transducer assembly, adapted for use with a control assembly, comprising:

a housing;

a transducer mounted in the housing wherein the transducer is operable to transmit ultrasonic energy along a path;

a connector having a first portion coupled to the transducer and the housing and a second portion coupled to the control assembly;

a passive thermal conductor mounted in the housing; and a liquid heat-transport fluid provided in a deformable bag contained within the housing and in thermal contact with the passive thermal conductor, wherein the deformable bag is positioned outside of the path.

68. A medical device, comprising:

a housing;

a transducer array, comprising a plurality of elements arranged in a plane; and a diamond-like carbon based material provided adjacent to the elements in thermal contact therewith.

69. The medical device of claim 68 further comprising an acoustic matching layer, wherein the diamond-like carbon material is provided as a thin film over the elements and wherein the film is located between the elements and the acoustic matching layer.

70. The medical device of claim 68 further comprising an acoustic backing material provided in the housing on a first side of the elements, wherein the diamond-like carbon material is provided as a thin film layer located between the elements and the acoustic backing material.

71. The medical device of claim 68 wherein the diamond-like carbon material is provided as a thin film layer over an acoustic matching layer provided on a side of the element plane.

72. The medical device of claim 68 further including at least one passive thermal conductor, wherein the diamond-like carbon is in thermal contact with the passive thermal conductor.

73. The medical device of claim 68 further including an active thermal conductor assembly, wherein the active thermal conductor assembly is in thermal contact with the diamond-like carbon.

74. A surgical method, comprising:

(a) providing a medical probe comprising a means for sensing array temperature, a transducer array having a field of view, and means for controlling the array temperature based on the output of said sensing means, wherein the controlling means is located outside of the field of view;

(b) acoustically imaging human tissue within the field of view by initiating a sonic pulse and detecting the reflection of said pulse;

(c) identifying, by evaluating said image, an affected area of human tissue; and (d) heating the affected area of tissue by energizing the transducer array said controlling means maintaining the array below a predetermined temperature.

75. The method of claim 74 wherein the controlling means further comprises a storage device and wherein the method comprises the additional step, after said step (c), of:

storing data representing a location of the affected area in the storage device.

76. The method of claim 74 further comprising:

identifying a plurality of affected areas; and heating each affected area.

77. A method as claimed in claim 74, further comprising the step of maintaining the array temperature at a predetermined level via the controlling means.

78. A method of cleaning an ultrasound probe having an ultrasound transducer mounted within a probe housing, comprising the steps of:

providing an active cooling device that is located within the probe housing, the device being thermally coupled to the ultrasound transducer;

applying an external source of heat to the probe housing; and actively cooling the ultrasound transducer during the application of the external source of heat by removing heat from the ultrasound transducer with the cooling device.

79. A method as claimed in claim 78, further comprising the steps of:

providing a thermal controller that is coupled to the active cooling device;

monitoring a temperature of the probe with the thermal controller; and actuating the active cooling device when the temperature reaches a predetermined setpoint.

80. A method as claimed in claim 79, further comprising the step of deactuating the active cooling device when the temperature reaches a second predetermined setpoint.

81. A method as claimed in claim 79, wherein the active cooling device has an adjustable heat removal capacity.

82. A method as claimed in claim 81, further comprising the step of adjusting the heat removal capacity of the active cooling device in accordance with the temperature.

83. A method as claimed in claim 78, wherein the active cooling device comprises a heat exchanger and a flowing coolant that is thermally coupled to the heat exchanger.

84. A method as claimed in claim 83, wherein the flowing coolant passes through a multi-pass, closed loop coolant path coupled to the heat exchanger.

85. A method as claimed in claim 78, wherein the active cooling device comprises an evaporative cooler.

86. A method as claimed in claim 78, wherein the active cooling device comprises a thermoelectric cooler.

87. A method as claimed in claim 78, wherein the step of applying an external source of heat to the probe housing comprises a hot disinfection procedure.

88. A method as claimed in claim 78, wherein the step of applying an external source of heat to the probe housing comprises a sterilization procedure.

89. In an ultrasound system having a probe that houses an ultrasound transducer for transmitting ultrasonic energy along a path, apparatus for protecting the probe during cleaning and cooling the probe during use, the apparatus comprising:

an active cooling device positioned outside of the path of the ultrasonic energy; and a thermal conduit coupling the active cooling device to the ultrasound transducer, wherein the thermal conduit is positioned outside of the path.

90. An apparatus as claimed in claim 89, further comprising a temperature sensor disposed within the probe, and a thermal controller coupled to the temperature sensor and the active cooling device.

91. An apparatus as claimed in claim 89, wherein the probe is attached to an ultrasound system console by a connector.

92. An apparatus as claimed in claim 91, wherein the active cooling device is disposed within the ultrasound system console.

93. An apparatus as claimed in claim 92, wherein the thermal conduit comprises a first conduit portion disposed within the ultrasound system console, a second conduit portion disposed within the probe, and a third conduit portion disposed within the connector, wherein the third conduit portion mates the first conduit portion to the second conduit portion.

94. An apparatus as claimed in claim 89, wherein the active cooling device comprises a heat exchanger and a flowing coolant that is thermally coupled to the heat exchanger.

95. An apparatus as claimed in claim 94, wherein the flowing coolant passes through a multi-pass, closed loop coolant path coupled to the heat exchanger.

96. An apparatus as claimed in claim 89, wherein the active cooling device comprises an evaporative cooler.

97. An ultrasound transducer assembly for use with a remote system console, comprising:

a transducer housing;

an ultrasound transducer mounted within the housing, the transducer operable to transmit a signal along a path; and an evaporator thermally coupled to the transducer for active heat transfer from the transducer;

a condenser; and a conduit coupling the evaporator to the condenser.

98. A transducer assembly as claimed in claim 97, further comprising a liquid disposed within the evaporator, wherein the liquid changes phase at a predetermined temperature.

99. A transducer assembly as claimed in claim 98, wherein the conduit comprises a vapor conduit connecting the evaporator to the condenser, and a liquid conduit connecting the condenser to the evaporator.

100. A transducer assembly as claimed in claim 99, wherein the evaporator, the condenser, the vapor conduit and the fluid conduit comprise a multi-pass, closed loop cooling system.

101. A transducer assembly as claimed in claim 97, further comprising an active cooling device thermally coupled to the condenser.

102. A method of controlling a temperature of an ultrasound probe having a transducer, comprising the steps of:

providing a device that is thermally coupled to the transducer;

providing a thermal controller that is coupled to the device;

monitoring a temperature of the probe with the thermal controller; and actuating the device when the temperature reaches a predetermined level.

103. A method as claimed in claim 102, further comprising the step of maintaining the probe at a predetermined setpoint by deactuating the device when the temperature falls below a second predetermined level.

104. A method as claimed in claim 102, wherein the device comprises a single pass, open loop cooling system.

105. An ultrasound transducer assembly, comprising:

a transducer housing;

an ultrasound transducer mounted within the housing, the transducer being operable to transmit a signal along a path; and an active cooling device thermally coupled to the ultrasound transducer and positioned in proximity to said transducer within the transducer housing outside of the signal path, wherein the cooling device comprises a single pass, open loop system said cooling device including a flowing coolant.

106. A transducer assembly as claimed in claim 105, wherein the coolant device comprises:

a heat exchanger thermally coupled to the ultrasound transducer;

an intake port;

an exhaust port; and a device for drawing a coolant from the intake port, through the heat exchanger, and out the exhaust port.

107. A transducer assembly as claimed in claim 106, wherein the coolant is a gas.

* * * * *